(12) United States Patent
Petit et al.

(10) Patent No.: US 8,007,792 B2
(45) Date of Patent: *Aug. 30, 2011

(54) ANTIBODIES DIRECTED AGAINST HEPATITIS C VIRUS E1E2 COMPLEX, COMPOSITIONS OF HCV PARTICLES, AND PHARMACEUTICAL COMPOSITIONS

(75) Inventors: Marie-Anne Petit, Bron (FR); Colette Jolivet-Reynaud, Saint Bonnet de Mure (FR); Christian Trepo, Lyons (FR)

(73) Assignees: INSERM, Paris (FR); Biomerieux SA, Marcy-l'Etoile (FR)

( * ) Notice: Subject to any disclaimer, the term of this patent is extended or adjusted under 35 U.S.C. 154(b) by 39 days.

This patent is subject to a terminal disclaimer.

(21) Appl. No.: 12/408,080

(22) Filed: Mar. 20, 2009

(65) Prior Publication Data
US 2009/0186023 A1    Jul. 23, 2009

Related U.S. Application Data

(62) Division of application No. 10/550,295, filed as application No. PCT/EP2004/003412 on Mar. 31, 2004, now Pat. No. 7,524,650.

(30) Foreign Application Priority Data

Apr. 1, 2003   (EP) ..................................... 03290822

(51) Int. Cl.
*A61K 39/395*   (2006.01)
(52) U.S. Cl. ............... 424/130.1; 424/133.1; 424/134.1; 424/135.1; 424/139.1; 424/149.1; 435/70.21
(58) Field of Classification Search .......................... None
See application file for complete search history.

(56) References Cited

U.S. PATENT DOCUMENTS 7,524,650 B2 *   4/2009   Petit et al. .................... 435/70.2

FOREIGN PATENT DOCUMENTS

| WO | WO 91/15574 | 10/1991 |
|----|-------------|---------|
| WO | WO 02/057314 A2 | 7/2002 |

OTHER PUBLICATIONS

Owens et al. (Journal of Immunological Methods, 1994, vol. 168, p. 149-165).*
Cocquerel Laurence et al:, "Recognition of native hepatitis C virus E1E2 heterodimers by a human monoclonal antibody.", Journal of Virology, vol. 77, No. 2, Jan. 20, 2003, pp. 1604-1609, XP002256295, ISSN:0022-538X, p. 1604-, right-hand column, line 6-plage 1605, right-hand coluimn, line 12.
Choukhi Amelie et al:, "Characterization of aggregates of hepatitis C virus glycoproteins.", Journal of General Virology, vol. 80, No. 12, Dec. 1999, pp. 3099-3107, XP002256296, ISSN: 0022-1317, p. 3101, left-hand column, line 24-right-hand column, line 12; figure 1.
Deleersnyder V et al: "Formation of Native Hepatitis C Virus Glycoprotein Complexes", Journal of Virology, The American Society for Microbiology, US, vol. 71, No. 1, 1997, pp. 697-704, XP002030792, ISSN: 0022-538X.
Fournillier A et al:, "Expression of noncovalent hepatitis C virus envelope E1-E2 complexes is not required for the induction of antibodies with neutralizing properties following DNA immunization", Journal of Virology, The American Society for Microbiology, US,, vol. 73, No. 9, Sep. 1999, pp. 7497-7504, XP002191425, ISSN: 0022-538X, abstract.
Seong Young Rim et al: "Immunogenicity of the E1E2 proteins of hepatitis C virus expressed by recombinant adenoviruses.", Vaccine, vol. 19, No. 20-22, 2001, pp. 2955-2964, XP0022569297, ISSN: 0264-410X, abstract.
Pumeechockchai W et al:, "Hepatitis C virus particles of different density in the blood of chronically infected immunocompetent and immunodeficient patients: Implications for virus clerance by antibody", Journal of Medical Virology, vol. 68. No. 3, Nov. 2002, pp. 335-342, XP008025913, ISSN: 0146-6615, p. 335, left-hand column, p. 337, left-hand column-right hand column, line 10, p. 340, left-hand column, paragraph 2-p. 341, rightr-hand column, last paragraphj.
Delpuech Oona et al:, "The hepatitis C virus (HCV) induces a long-term increase of interleukin-10 production b y human CD4+ T cells (H9)", European Cytokine Network, vil. 12, No. 1, Mar. 2001, pp. 70, left-hand column, last paragraph-right-hand column, paragraph 1.
Bartosch Birke et al: "Infectious hepatitis C virus pseudo-particles containing functional E1-E2 envelope protein complexes.", Journal of Experimental Medicine, vol. 197. No. 5, Mar. 3, 2003 92003-03-03), pp. 633-642, XP002267924, ISSN: 0022-1007, p. 633, left-hand column, line 1 right-hand column, line 1; figure 2.
Grant P R et al:, "Quantification of HCV RNA levelsw and detection of core antigen in donations before seroconversion", Transfusion (Bethesda), vol. 42, No. 8, Aug. 2002, pp. 1032-1036, XP001174198, ISSN: 0041-1132, p. 1034, right-hand column, line 16-line 24.
Lechmann et al., Hepatology, 2001, vol. 34, p. 417-423.
Journal of Biochemical Chemistry, Nov. 2003, vol. 278, p. 44385-44392.

* cited by examiner

*Primary Examiner* — Agnieszka Boesen
(74) *Attorney, Agent, or Firm* — Young & Thompson

(57) ABSTRACT

New conformational antibodies are directed against HCV and more particularly to monoclonal antibodies. Described compositions of particles are liable to be recognized by the antibodies, as are pharmaceutical compositions containing them. Also described are HCV enveloped subviral particles or purified HCV enveloped complete viral particles, and the processes for preparing them.

4 Claims, 17 Drawing Sheets

SEQUENCE LISTING

```
<160> NUMBER OF SEQ ID NOS: 28

<210> SEQ ID NO 1
<211> LENGTH: 10
<212> TYPE: PRT
<213> ORGANISM: Hepatitis C virus

<400> SEQUENCE: 1

Arg His Trp Thr Thr Gln Gly Cys Asn Cys
 1               5                  10

<210> SEQ ID NO 2
<211> LENGTH: 15
<212> TYPE: PRT
<213> ORGANISM: Hepatitis C virus

<400> SEQUENCE: 2

Pro Asp Gln Arg Pro Tyr Cys Trp His Tyr Pro Pro Lys Pro Cys
 1               5                  10                  15

<210> SEQ ID NO 3
<211> LENGTH: 9
<212> TYPE: PRT
<213> ORGANISM: Hepatitis C virus

<400> SEQUENCE: 3

Tyr Arg Leu Trp His Tyr Pro Cys Thr
 1               5

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 4

Cys Cys Cys Thr Cys Ala Thr Ala Gly Thr Thr Ala Gly Cys Gly Thr
 1               5                  10                  15

Ala Ala Cys Gly
            20

<210> SEQ ID NO 5
<211> LENGTH: 20
<212> TYPE: PRT
<213> ORGANISM: Hepatitis C virus

<400> SEQUENCE: 5

Gln Leu Phe Thr Phe Ser Pro Arg Arg His Trp Thr Thr Thr Gln Gly
 1               5                  10                  15

Cys Asn Cys Ser
            20
```

-continued

```
<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Pro Leu Arg His Tyr Glu Leu Pro Leu Ile Gln
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Pro His Asn His Ser Thr His Ser Arg Thr His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Pro Lys Tyr His Pro Arg Phe His Lys His Ala
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gln Arg Ser Arg His Trp His Asp Val Pro Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ser Gln Pro Arg Trp His Gln Lys Pro Ala Thr
1               5                   10

<210> SEQ ID NO 11
<211> LENGTH: 21
<212> TYPE: PRT
<213> ORGANISM: Hepatitis C virus

<400> SEQUENCE: 11

Ala Ile Leu Asp Met Ile Ala Gly Ala His Trp Gly Val Leu Ala Gly
1               5                   10                  15
```

```
Ile Ala Tyr Phe Ser
            20

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Lys Met Pro Arg Ala Thr Asp Trp Asn Leu Arg
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Trp Gly Asn His Ser Lys Ser His Pro Gln Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp His Arg Thr Pro Ser Thr Leu Trp Gly Val Ile
1               5                   10

<210> SEQ ID NO 15
<211> LENGTH: 21
<212> TYPE: PRT
<213> ORGANISM: Hepatitis C virus

<400> SEQUENCE: 15

Asp Gln Arg Pro Tyr Cys Trp His Tyr Pro Pro Lys Pro Cys Gly Ile
1               5                   10                  15

Val Pro Ala Lys Ser
            20

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp His Lys Leu Pro Gly His Pro Arg Thr Val
1               5                   10

<210> SEQ ID NO 17
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 17

Thr Phe Ala Trp His Lys Pro Arg Val Asn Leu Gly
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Ser Ser Trp Tyr Ile Gln His Phe Pro Pro Leu
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Pro Ala His Pro Leu Pro Arg Leu Pro Ser Leu
 1               5                  10

<210> SEQ ID NO 20
<211> LENGTH: 22
<212> TYPE: PRT
<213> ORGANISM: Hepatitis C virus

<400> SEQUENCE: 20

Asp Tyr Pro Tyr Arg Leu Trp His Tyr Pro Cys Thr Ile Asn Tyr Thr
 1               5                  10                  15

Ile Phe Lys Ile Arg Met
            20

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp His Trp Asn Lys Pro Ile Ile Arg Pro Pro Leu Arg
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Pro Tyr Lys Leu Gln Ala Ala Ala Thr Leu Tyr
 1               5                  10

<210> SEQ ID NO 23
```

```
<211> LENGTH: 14
<212> TYPE: PRT
<213> ORGANISM: Hepatitis C virus

<400> SEQUENCE: 23

Leu Ser Thr Gly Leu Ile His Leu His Gln Asn Ile Val Asp
 1               5                  10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

His Leu Tyr His Lys Asn Arg Asn His His Ile Ala Tyr
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Ser Pro Gly Gln Gln Arg Leu His Asn Ser Thr
 1               5                  10

<210> SEQ ID NO 26
<211> LENGTH: 8
<212> TYPE: PRT
<213> ORGANISM: Hepatitis C virus

<400> SEQUENCE: 26

Gly Pro Asp Gln Arg Pro Tyr Cys
 1               5

<210> SEQ ID NO 27
<211> LENGTH: 8
<212> TYPE: PRT
<213> ORGANISM: Hepatitis C virus

<400> SEQUENCE: 27

Trp His Tyr Pro Pro Lys Pro Cys
 1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 28

Trp His Tyr Pro
 1
```

ANTIBODIES DIRECTED AGAINST HEPATITIS C VIRUS E1E2 COMPLEX, COMPOSITIONS OF HCV PARTICLES, AND PHARMACEUTICAL COMPOSITIONS

This application is a divisional application of Ser. No. 10/550,295, filed Feb. 23, 2006, currently pending, which claims priority to PCT/EP2004/003412, filed Mar. 31, 2004, which claims priority to European Application No. 03 290 822.0, filed Apr. 1, 2004. The teachings of the above applications are hereby incorporated by reference. The entire contents of each of the above-identified applications are hereby incorporated by reference.

BACKGROUND OF THE INVENTION

1. Field of the Invention

The present invention relates to new conformational antibodies directed against HCV and more particularly to monoclonal antibodies. The invention also relates to compositions of particles liable to be recognized by said antibodies, and to pharmaceutical compositions containing them. The invention also relates to HCV enveloped subviral particles or purified HCV enveloped complete viral particles, and the processes for preparing them.

2. Description of the Related Art

Hepatitis C Virus (HCV) infection is a major cause of chronic hepatitis and cirrhosis and may lead to hepatocellular carcinoma. With about 200 million people worldwide chronically infected with HCV, this disease has emerged as a serious global health problem. HCV is an enveloped RNA virus belonging to the genus Hepacivirus of the Flaviridae family. Its genome is a 9.6-kb single-stranded RNA of positive polarity with a 5' untranslated region (UTR) that functions as an internal ribosome entry site, a single open reading frame encoding a polyprotein of approximately 3,000 amino acids and a 3'UTR (Bartenschlager et al., 2000). This polyprotein is co- and post-translationally cleaved by host cell peptidases to yield the structural proteins including the core protein and the envelope glycoproteins E1 and E2, and by viral proteases to generate the non-structural proteins (NS) 2 to 5B (Bartenschlager et al., 2000). By analogy to related positive-strand RNA viruses, replication occurs by means of a negative-strand RNA intermediate and is catalyzed by the NS proteins, which form a cytoplasmic membrane-associated replicase complex.

The low levels of HCV particles present in patient plasma samples and the lack of a cell culture system supporting efficient HCV replication or particle assembly have hampered the characterization of the glycoproteins associated with the virion. The current knowledge on HCV envelope glycoproteins is based on cell culture transient-expression assays with viral or non viral expression vectors. These studies have shown that the E1 and E2 glycoproteins interact to form complexes (reviewed in Dubuisson, 2000). In the presence of nonionic detergents, two forms of E1E2 complexes are detected: an E1E2 heterodimer stabilized by noncovalent interactions and heterogeneous disulfide-linked aggregates, which are considered to represent misfolded complexes. Previously, envelope glycoprotein-specific antibodies have been obtained by immunization with synthetic peptides or recombinant antigens. A conformation sensitive E2-reactive monoclonal antibody (mAb) (H2), which recognizes noncovalently-linked E1E2 heterodimers considered as the native prebudding form of the HCV glycoprotein heterodimer, however does not react with serum-derived HCV RNA-positive particles (Deleersnyder et al., 1997). Furthermore, WO 92/07001 discloses antibodies which have been prepared by immunization of mice with a preparation of HCV particles extracted from infected chimpanzees, however these antibodies have not been tested on natural HCV particles (i.e. derived from infected patients). Moreover, WO 00/05266 discloses antibodies prepared from infected patients B cells, however these antibodies have been selected according to their ability to bind to the recombinant E2 protein. Therefore, all these antibodies are of limited use, either for diagnostic purposes, or for therapeutic or prophylactic purposes, as they have been produced or selected with unnatural HCV, or parts thereof, and have not been shown to interact with natural HCV particles.

The lack of HCV preparation containing natural enveloped HCV particles in sufficient quantity and concentration, is one of the reason for which antibodies liable to recognize natural HCV particles could not be obtained so far. In fact, low levels of HCV particles in plasma samples have made characterization and visualization of this virus difficult. Previously, it has been shown that virus recovered during the acute phase of infection from the plasma of naturally infected patients has a buoyant density of approximately 1.06 g/ml in sucrose (Hijikata et al., 1993). In contrast, HCV recovered from cell culture after replication in vitro has a buoyant density of 1.12 g/ml in sucrose (Yoshikura et al., 1996). Finally, HCV recovered from chronically infected individuals has a buoyant density of approximately 1.17 g/ml in sucrose (Hijikata et al., 1993). The low density of the serum-derived virus has been ascribed to its association with serum low-density lipoproteins (Thomssen et al., 1992). The high density virus has been shown to be associated with antibody bound to the virus in antigen-antibody complexes (Kanto et al., 1995). In spite of these data, there is as yet no indication on the protein composition of these different HCV populations, and whether low density fractions (<1.0 g/ml) contained envelope, RNA and nucleocapsid as complete virions.

BRIEF SUMMARY OF THE INVENTION

Thus, an object of the invention is to provide antibodies which react with natural HCV particles.

Another aspect of the invention is to provide compositions of natural HCV particles, in sufficient quantity and concentration to allow efficient immunization of antibody producing animals.

Another aspect of the invention is to provide specific HCV compositions devoid of infectivity, liable to be used as active substances of pharmaceutical compositions.

DETAILED DESCRIPTION OF THE INVENTION

The present invention relates to a conformational antibody capable of specifically binding to the natural HCV viral envelope.

The expression "conformational antibody" designates an antibody which recognizes an epitope having a three-dimensional structure defined by its molecular surrounding.

The expression "specifically binding" means that the antibody binds to an epitope which is found on substantially only one of the elements forming the natural HCV viral envelope, that is to say that there is substantially no binding of the antibody with elements other than the elements forming the natural HCV envelope. For example, the binding specificity of the antibody can be tested by methods well known to the man skilled in the art, such as Western blotting experiments, wherein biological samples are electrophoretically migrated on a gel, then transferred on a membrane and co-incubated with said antibody, which is then detected by a secondary antibody. Said antibody is said to be "specifically binding" to a target compound contained in said biological samples if substantially all of the electrophoretical bands detected contain the target compound or parts thereof.

"HCV" means "hepatitis C virus", it is in particular described in Choo et al. (1989, 1991). HCV particularly comprises RNA, a capsid made of a core protein, and an envelope which comprises lipids and proteins, particularly glycoproteins.

The "HCV viral envelope" is made of lipids and proteins, in particular glycoproteins such as HCV proteins E1 and E2 (Clarke, 1997).

"Natural" means that HCV, or parts thereof, are as found in biological samples and possibly as isolated and if needed as purified from biological samples. Such samples may be blood, plasma or sera, of patients infected by HCV. In particular, "natural" refers to HCV, or parts thereof, which have not been produced by recombinant methods, or by using cell lines or animals, and are different from HCV elements described in Schalich et al. (1996), Blanchard et al., (2002) or WO 92/07001 for instance.

The present invention more particularly relates to a conformational antibody capable of specifically binding to the natural HCV E2 protein.

HCV E2 is in particular described in Dubuisson (2000) and Op De Beeck et al. (2001). It is produced as a polyprotein (3012 amino acids) which is cleaved to yield E2 (amino acids 384 to 714).

The expression "specifically binding" means that the antibody binds to an epitope, or a part thereof, which is found on substantially only the HCV E2 protein. In particular the antibody can not be detached from the HCV E2 protein in competition tests, wherein the antibody-E2 complex is presented with other proteins.

The expression "natural HCV E2 protein" means that the protein is as found in biological samples of patients infected by HCV, in particular the natural HCV E2 protein is not a recombinant protein.

The present invention relates to a conformational antibody as defined above, capable of neutralizing HCV infections in patients.

"Neutralizing HCV infection" means that the antibody is capable of improving the health of patients infected by HCV, as can be evidenced, for instance, by the diminishing of HCV detected in blood, plasma or sera, or that the antibody is capable of preventing individuals to be infected by HCV The HCV infection neutralization capability of said antibody can be monitored in model animals, such as chimpanzees or mice, in particular humanized mice, which are chronically infected by HCV, or which are primo-infected by HCV in presence of said antibody. The monitored antibody should be capable of respectively inducing a diminishing of HCV related viremia or to prevent infection by HCV.

The present invention relates to a conformational antibody as defined above, capable of precipitating the HCV E1E2 complex under its covalent or non covalent forms.

The HCV E1E2 complex may be non covalent, that is to say that E1 and E2 are associated by means of weak bonds, such as hydrogen bonding, ionic bonding, Van Der Waals bonding or hydrophobic bonding, or covalent, that is to say that E1 and E2 are associated by means of covalent bonds, such as disulfure bonds for instance. Covalent and non-covalent forms of the E1E2 complex are in particular described or suggested in Deleersnyder et al. (1997).

"Precipitating" means that the antibody may render the HCV E1E2 complex insoluble. Precipitation may occur for instance such as described by Dubuisson and Rice (1996).

The present invention relates to a conformational antibody as defined above, capable of specifically binding to the natural HCV E1 protein.

HCV E1 is in particular described in Dubuisson (2000) and Op De Beeck et al. (2001). It is produced as a poly-protein (3012 amino acids) which is cleaved to yield E1 (amino acids 192 to 383).

The expression "specifically binding" means that the antibody binds to an epitope, or a part thereof, which is found on substantially only the HCV E1 protein. In particular the antibody can not be detached from the HCV E1 protein in competition tests, wherein the antibody-E1 complex is presented with other proteins.

The expression "natural HCV E1 protein" means that the protein is as found in biological samples of patients infected by HCV, in particular the natural HCV E1 protein is not a recombinant protein.

The present invention more specifically relates to a conformational antibody, capable of specifically binding to the natural HCV E1 protein, to the natural HCV E2 protein, and of precipitating the HCV E1E2 complex under its covalent or non covalent forms.

The present invention relates to a conformational antibody as defined above, capable of specifically binding to an epitope constituted of at least one of the following sequences:
  amino acids 297 to 306 of HCV protein E1;
  amino acids 480 to 494 of HCV protein E2;
  amino acids 613 to 621 of HCV protein E2.

The antibody according to the invention is able to bind to:
  a molecule presenting a peptide comprising amino acids 297 to 306 of HCV protein E1, corresponding to the following sequence: RHWTTQGCNC (SEQ ID NO: 1); and/or
  to a molecule presenting a peptide comprising amino acids 480 to 494 of HCV protein E2, corresponding to the following sequence: PDQRPYCWHYPPKPC (SEQ ID NO: 2); and/or
  to a molecule presenting a peptide comprising amino acids 613 to 621 of HCV protein E2, corresponding to the following sequence: YRLWHYPCT (SEQ ID NO: 3).

The binding of said antibody to at least one of the preceding sequences can be tested by synthesising a peptide containing any of the preceding sequences and by assaying the antibody binding capability to said synthesised peptide by methods well known to the man skilled in the art, such as ELISA or EIA for example.

The acronym "ELISA" means Enzyme Linked Immuno Sorbent Assay.

The acronym "EIA" means Enzyme Immunoassay.

The present invention relates to a conformational antibody as defined above, capable of specifically binding to an epitope constituted of each of the following sequences:
  amino acids 297 to 306 of HCV protein E1;
  amino acids 480 to 494 of HCV protein E2;
  amino acids 613 to 621 of HCV protein E2.

The antibody according to the invention is able to bind to a molecule presenting an epitope, said epitope comprising;
  a peptide comprising amino acids 297 to 306 of HCV protein E1, corresponding to the following sequence: RHWTTQGCNC (SEQ ID NO: 1); and
  a peptide comprising amino acids 480 to 494 of HCV protein E2, corresponding to the following sequence: PDQRPYCWHYPPKPC (SEQ ID NO: 2); and a peptide comprising amino acids 613 to 621 of HCV protein E2, corresponding to the following sequence: YRLWHYPCT (SEQ ID NO: 3).

The binding of said antibody to an epitope comprising each of the preceding sequences can be tested by assaying the antibody binding capability to a molecule, in particular a protein, which comprises the sequence RHWTTQGCNC (SEQ ID NO: 1), and to a molecule, in particular a protein, which comprises the sequence PDQRPYCWHYPPKPC (SEQ ID NO: 2), and to a molecule, in particular a protein, which comprises the sequence YRLWHYPCT (SEQ ID NO: 3), by methods well known to the man skilled in the art, such as ELISA or EIA for example.

The present invention relates to a conformational antibody as defined above, wherein said antibody is a monoclonal antibody.

The expression "monoclonal antibody" means that the antibody binds to substantially only one epitope, or to parts of said epitope.

A monoclonal antibody can be obtained from monoclonal cell lines, derived from immortalized antibody secreting cells, such as hybridomas for instance.

Monoclonal cell lines are derived from the culturing of a unique cell.

A hybridoma can be produced by fusion of an antibody secreting cell, such as a B cell, with an immortalized cell, according to Kohler and Milstein (1975) or to Buttin et al. (1978) for example.

According to another aspect of the invention, a monoclonal antibody as defined above is secreted by the hybridoma deposited under the Budapest Treaty at the CNCM (Collection Nationale de Culture de Microorganismes, Institut Pasteur, Paris, France) on Mar. 19, 2003, under accession number CNCM I-2983.

Said monoclonal antibody in particular binds to the natural HCV viral envelope, to the natural HCV E2 protein, to the natural HCV E1 protein, and is capable of precipitating the HCV E1E2 complex under its covalent or non covalent forms, and is capable of binding to an epitope constituted of at least one or of all of the above-defined sequences. Said monoclonal antibody is in particular referred to hereafter as D32.10.

According to another aspect of the invention, a monoclonal antibody as defined above is secreted by the hybridoma deposited under the Budapest Treaty at the CNCM (Collection Nationale de Culture de Microorganismes, Institut Pasteur, Paris, France) on Mar. 19, 2003, under accession number CNCM I-2982.

Said monoclonal antibody in particular binds to the natural HCV viral envelope and to the HCV E2 protein. Said monoclonal antibody is in particular referred to hereafter as D4.12.9.

The invention also relates to fragments or derivatives of the antibodies according to the invention. Fragments of the antibodies of the invention in particular encompass Fab, $F(ab')_2$ or scFv (single-chain Fv) fragments, which are well known to the man skilled in the art. Derivatives of the antibodies of the invention comprise, if appropriate, humanized antibodies. Humanized antibodies can be for example chimeric antibodies, in which, if appropriate, parts of the antibodies according to the invention are replaced by the complementary determining region (CDR) of the antibodies according to the invention, can be grafted to human antibodies, such as described for instance in U.S. Pat. No. 5,824,307.

According to another embodiment, the invention relates to a hybridoma deposited under the Budapest Treaty at the CNCM (Collection Nationale de Culture de Microorganismes, Institut Pasteur, Paris, France) on Mar. 19, 2003, under accession number CNCM I-2983.

According to another embodiment, the invention relates to a hybridoma deposited under the Budapest Treaty at the CNCM (Collection Nationale de Culture de Microorganismes, Institut Pasteur, Paris, France) on Mar. 19, 2003, under accession number CNCM I-2982.

According to another embodiment, the invention relates to a pharmaceutical composition comprising as active substance at least one of the antibodies as defined above and a pharmaceutically acceptable vehicle.

A pharmaceutically acceptable vehicle is in particular as defined in Remington's Pharmaceutical Sciences $16^{th}$ ed./Mack Publishing Co.

Other compounds, in particular antiviral compounds can be included in the above defined composition, such as other anti-HCV antibodies and fragments or derivatives thereof, interferons, RNA polymerase inhibitors, protease inhibitors or helicase inhibitors.

The above mentioned pharmaceutical composition can be administered in a single dose or multiple doses. In case of a single dose, the composition may comprise from about 0.1 mg of antibody per kg of body weight, to about 1 g of antibody per kg of body weight, in particular from about 1 mg/kg to about 100 mg/kg. In case of multiple doses, the composition can be administered in a dosage of about 0.1 mg of antibody per kg of body weight per day, to about 1 g of antibody per kg of body weight per day, in particular from about 1 mg/kg/day to about 100 mg/kg/day.

According to another embodiment, the invention relates to the use of at least one of the antibodies as defined above, for the preparation of a medicament for the diagnostic, the prevention or the treatment of HCV infections.

The antibodies according to the invention can be used for the detection of HCV viral particles in biological samples liable to contain HCV. Such samples may be obtained from patients infected by HCV or at risk of being infected by HCV and comprises in particular samples of blood, plasma or serum. Any of the methods well known of the man skilled in the art for the detection of viruses with antibodies, such as ELISA or EIA, can be applied with the antibodies of the invention.

The antibody according to the invention can be used for the preparation of a medicament administered to patients infected or not with HCV, to neutralize HCV infection. HCV infection neutralization can proceed by preventing HCV from contacting target cells, for instance by binding the antibody to envelope molecules, such as E1 or E2, which bind to target cells membrane receptors, thereby preventing the HCV-target cells binding.

The antibody can be administered to patients infected by HCV to prevent HCV viral particles from infecting cells, in particular hepatocytes, or to promote capture of HCV coated with said antibodies by cells of the immune system.

The antibody can in particular be administered to patients which are to receive a transplanted organ, in particular a liver, prior, during or after the transplantation surgery, to neutralize HCV viral particles which may be contained in the transplanted organ.

The invention also relates to an enveloped viral particle capable of binding to at least one of the antibodies as defined above.

The expression "enveloped viral particle" represents in particular a HCV virion, or part of a HCV virion, which contains an envelope, the envelope comprising lipids and/or proteins, in particular glycoproteins, associated in leaflets.

The invention also relates to an antibody which binds to an enveloped viral particle capable of binding to at least one of the antibodies as defined above.

According to another embodiment, the invention relates to a composition of HCV viral particles derived from initial samples of human blood, plasma or sera, wherein the concentration of HCV RNA copies is about 100 to 1000 fold higher than the concentration of HCV RNA copies in the initial samples of human, blood, plasma or sera from which it is derived, and is in particular higher than about $10^7$ copies/ml.

The high concentration of the compositions according to the invention allows efficient immunization of animals with said compositions.

HCV RNA is in particular HCV genomic RNA.

The HCV RNA contents of a sample can be measured by RT-PCR, in particular quantitative RT-PCR, with the Amplicor™ HCV Monitor™, Roche Diagnostics (Young et al., 1993) for example.

Alternatively, the HCV RNA contents of a sample can also be measured using the NASBA (Nucleic Acid Sequence Based Amplification) technology (Damen et al., 1999).

The HCV RNA contents of a sample can be expressed in terms of number of copies of HCV RNA molecules in said sample, one copy being equivalent to one International Unit (UI).

The HCV RNA contents of a sample is indicative of the quantity HCV virions contained in said sample.

A composition containing more than about $10^7$ copies/ml of HCV RNA allows efficient immunization of animals with said composition.

The invention more specifically relates to a composition as defined above, wherein the number of HCV RNA copies is from about $10^8$ to about $10^9$ UI per mg of protein.

The protein content of the composition is assessed by methods well known to the man skilled in the art, and particularly by the Lowry assay (Lowry et al., 1951) such as the Biorad protein assay (Biorad Laboratories).

This measure represents the specific activity of the composition, it is indicative of the purity of the composition; the higher the number of HCV RNA copies per mg of protein the higher the purity of the HCV containing composition.

The invention further relates to a composition as defined above, wherein the volume of said composition is from about 0.1 ml to about 10 ml.

A composition volume of about 0.1 ml to about 10 ml corresponds to a composition as defined above containing at least $10^6$ HCV RNA copies.

Such a composition is useful for the immunization of animals. For example, the efficient immunization of a mouse requires the administration of a HCV viral particles composition containing more than about $10^6$ HCV RNA copies, as described in the examples.

According to another embodiment the invention relates to an isolated HCV enveloped subviral particle substantially devoid of HCV RNA and of HCV core protein.

The term "isolated" means that the particle has been extracted from its natural environment, it has in particular been separated from other HCV viral particles or parts thereof which contain HCV RNA and/or HCV core protein.

The expression "substantially devoid of HCV RNA and of HCV core protein" means that the solution containing the above defined subviral particle contains less than $10^4$ UI/ml of HCV RNA as measured with Amplicor™ HCV Monitor™, Roche Diagnostics (Young et al., 1993), and less than 1 pg/ml of core protein as measured with the Ortho-Clinical Diagnostics test (Aoyagi et al., 1999).

The presence of the envelope can be assessed for instance by an EIA or an ELISA test with the antibody secreted by the hybridoma deposited at the CNCM under accession number 1-2983, hereafter named D32.10, or the antibody secreted by the hybridoma deposited at the CNCM under accession number I-2982, hereafter named D4.12.9.

The expression "HCV enveloped subviral particle" means that the particle contains substantially only the envelope part of the HCV virion, that is to say lipids and proteins, in particular glycoproteins, associated in leaflets. HCV viral particles isolated thus far either contained HCV RNA and/or HCV core protein.

The invention more specifically relates to an isolated HCV enveloped subviral particle as defined above, wherein said subviral particle is liable to bind to any of the antibodies as defined above.

The binding of the above defined subviral particle to the antibodies of the invention can be assessed by several methods well known to the man skilled in the art, such as immunoprecipitation, ELISA, EIA or Western blotting for example.

According to another embodiment, the invention relates to a composition comprising purified HCV enveloped complete viral particles, said purified HCV enveloped complete viral particles containing HCV RNA, HCV core protein and HCV envelope, and being liable to bind to any of the antibodies as defined above.

The invention more particularly relates to a composition comprising purified natural HCV enveloped complete viral particles.

The expression "HCV enveloped complete viral particles" means that HCV virions contain HCV genomic RNA, HCV core protein and HCV envelope. There has been no report in the prior art of a HCV viral particle containing these three components.

The presence of HCV RNA, HCV core protein and HCV envelope can assessed by using the methods as defined above.

The term "purified" means that the above defined HCV enveloped complete viral particle has been separated from other compounds, such as HCV enveloped subviral particles. In particular, it can be assessed, for example by electron microscopy, that the composition contains 90% less HCV enveloped subviral particles than HCV enveloped complete viral particles.

The binding of the above defined HCV enveloped complete viral particle to the antibodies according to the invention can be assessed by several methods well known to the man skilled in the art, such as immunoprecipitation, ELISA, EIA or Western blotting for example.

According to another embodiment, the invention relates to a process for preparing a composition of HCV viral particles comprising the following steps:

at least two ultracentrifugations of a sample resulting from a clarified plasmapheresis of a HCV infected patient to obtain a HCV enriched pellet;

resuspension of the HCV enriched pellet in an aqueous solution to obtain a composition of HCV viral particles.

The ultracentrifugations may be carried out for instance at a speed of about 190,000 g to about 220,000 g, preferably 210,000 g, during about 3 hours to about 5 hours, preferably 4 hours.

The preferred centrifugation conditions lead to precipitation of viral particles, such as HCV viral particles, while other compounds contained in the clarified plasma are not precipitated.

The term "plasmapheresis" means that the patient's blood has been filtered to obtain plasma while the remainder of the blood has been re-injected to the patient.

The term "clarified" means that the plasma obtained from the plasmapheresis has been centrifuged at low speed, in particular at 3000 g during 30 minutes.

The initial volume of plasmapheresis before ultracentrifugation is advantageously of about 1 liter.

According to another embodiment, the invention relates to a composition of HCV viral particles such as obtained according to the above-mentioned process for preparing a composition of HCV viral particles.

According to another embodiment, the invention relates to a process for preparing a composition of HCV enveloped subviral particles comprising the following steps:
  at least two ultracentrifugations of a sample resulting from a clarified plasmapheresis of a HCV infected patient to obtain a HCV enriched pellet;
  resuspension of the HCV enriched pellet in an aqueous solution;
  ultracentrifugation of the resuspended HCV enriched pellet in a sucrose density gradient to separate the elements of the resuspended HCV enriched pellet into fractions according to their density;
  recovery of the fractions containing substantially no HCV RNA, substantially no HCV core protein and containing particles capable of binding to the monoclonal antibody defined above as D32.10 or D4.12.9, to obtain a composition of HCV enveloped subviral particles.

The ultracentrifugation of the resuspended HCV enriched pellet in a sucrose density gradient maybe carried out from about 190,000 g to about 220,000 g, preferably 210,000 g, during about 40 hours to about 50 hours, preferably 48 hours, the sucrose gradient can be advantageously from about 10% to about 60% w/w, from about 20 to about 50% w/w, from about 25% to about 45% w/w, or from about 30% to about 45% w/w.

All the fractions obtained are tested for the presence of HCV RNA, HCV core protein and/or particles capable of binding to D32.10 or D4.12.9.

The fractions are said to contain substantially no HCV RNA when the content of HCV RNA as measured by Amplicor™ HCV Monitor™, Roche Diagnostics (Young et al., 1993), is less than about $10^4$ UI/ml.

The fractions are said to contain substantially no HCV core protein when the content of HCV core protein as measured by the Ortho-Clinical Diagnostics test (Aoyagi et al., 1999) is less than about 1 pg/ml.

The monoclonal antibody used is in particular the monoclonal antibody D32.10 which is secreted by the hybridoma deposited at the CNCM under accession number I-2983

The particles are said capable of binding to the above mentioned monoclonal antibody if they can be tested positive in the following EIA test:

Polystyrene plates of 96-wells (Falcon; Becton Dickinson France S. A, Le Pont de Claix) are coated with the different fractions diluted from $10^{-1}$ to $10^{-4}$. The plates are incubated overnight at 4° C. and are then saturated with Tris-NaCl (TN) buffer (20 mM Tris-HCl, pH 7.5 and 100 mM NaCl) containing 5% (w/v) bovine serum albumin (BSA). mAb D32.10 diluted in a mixture of TN/BSA buffer and 50% normal human serum (NHS) at a concentration of 5 µg/ml is added to each well and incubated for 2 h at 37° C. The bound antibody is detected with a horseradish peroxidase (HRPO)-conjugated F(ab')2 fragment of anti-mouse immunoglobulins (diluted 1/5,000; Immunotech) and with orthophenylenediamine (OPD) and hydrogen peroxide ($H_2O_2$) as substrates. Optical density (OD) is determined at 450 nm or at 490 nm with an ELISA plate reader (MRX, Dynex). The results are considered as positive when superior to cut-off, corresponding to mean of negative controls multiplied by 2.1.

The recovered fractions have in particular a sucrose density of approximately 1.13 to 1.15 g/ml.

Alternatively, the fractions are first tested for the presence of particles capable of binding to D32.10 and/or D4.12.9, if substantially no such particles are present, then no other test is performed, if such particles are present, then the HCV RNA test and/or the HCV core protein test are performed.

According to another embodiment, the invention relates to a composition of HCV enveloped subviral particles such as obtained according to the above process for preparing a composition of HCV enveloped subviral particles.

According to another embodiment, the invention relates to a process for preparing a composition of purified HCV enveloped complete viral particles comprising the following steps:
  at least two ultracentrifugations of a sample resulting from a clarified plasmapheresis of a HCV infected patient to obtain a HCV enriched pellet;
  resuspension of the HCV enriched pellet in an aqueous solution;
  ultracentrifugation of the resuspended HCV enriched pellet in a sucrose density gradient to separate the elements of the resuspended HCV enriched pellet into fractions according to their density;
  recovery of the fractions containing from about $5.10^5$ to about $10^6$ UI of HCV RNA per ml, from about 50 to about 100 pg of HCV core protein per ml, and containing particles capable of binding to the monoclonal antibody defined above as D32.10 or D4.12.9, to obtain a composition of purified HCV enveloped complete viral particles.

The ultracentrifugation of the resuspended HCV enriched pellet in a sucrose density gradient maybe carried out from about 190,000 g to about 220,000 g, preferably 210,000 g, during about 40 hours to about 50 hours, preferably 48 hours, the sucrose gradient can be advantageously from about 10% to about 60% w/w, from about 20 to about 50% w/w, from about 25% to about 45% w/w, or from about 30% to about 45% w/w.

HCV RNA content, HCV core protein content and the binding capability of the particles are measured as indicated above.

The monoclonal antibody used is in particular the monoclonal antibody D32.10 which is secreted by the hybridoma deposited at the CNCM under accession number I-2983.

The composition obtained by this process contains in particular purified HCV enveloped complete viral particles and is in particular substantially devoid of HCV enveloped subviral particles. In particular, it can be assessed, for example by electron microscopy, that the composition contains 90% less HCV enveloped subviral particles than HCV enveloped complete viral particles.

The recovered fractions have in particular a sucrose density of approximately 1.17 to 1.21 g/ml, more particularly of approximately 1.17 to 1.20 g/ml, of approximately 1.19 to 1.21 g/ml, of approximately 1.17 to 1.19 g/ml, or of approximately 1.19 to 1.20 g/ml.

Alternatively, the fractions are first tested for the presence of HCV RNA, if more than $10^5$ copies/ml of HCV RNA are present, then the HCV core protein test is performed, if more than 50 pg/ml of core protein are present, then the presence of particles capable of binding to D32.10 and/or to D4.12.9 is tested; if less than $10^5$ copies/ml of HCV RNA are present then no other test is performed.

According to another embodiment, the invention relates to a composition of purified HCV enveloped complete viral particles such as obtained according to the above corresponding process.

The invention also relates to a process for preparing a monoclonal antibody secreted by the hybridoma deposited at the CNCM under accession number I-2983, comprising the following steps:
- immunizing an animal, in particular a mammal, with a composition of HCV viral particles of the invention, or such as prepared according to the invention, and recovering the generated antibodies;
- selecting, among the generated antibodies, monoclonal antibodies on their ability of binding to the HCV viral particles contained in the above mentioned composition of HCV viral particles.

The composition of HCV viral particles can be obtained as follows:
- at least two ultracentrifugations of a sample resulting from a clarified plasmapheresis of a HCV infected patient to obtain a HCV enriched pellet;
- resuspension of the HCV enriched pellet in an aqueous solution to obtain a composition of HCV viral particles.

The selection of the generated antibodies can be carried out with an indirect EIA test as defined above, the plates being coated with the composition of HCV viral particles of the invention.

According to another embodiment, the invention relates to a process for preparing a monoclonal antibody secreted by the hybridoma deposited at the CNCM under accession number I-2982, comprising the following steps:
- immunizing an animal, in particular a mammal, with a composition of purified HCV enveloped complete viral particles of the invention, or such as prepared according to the invention, and recovering the generated antibodies;
- selecting, among the generated antibodies, monoclonal antibodies on their ability of binding to the purified HCV enveloped complete viral particles contained in the above mentioned composition of purified HCV enveloped complete viral particles.

The composition of purified HCV enveloped complete viral particles can be obtained as follows:
- at least two ultracentrifugations of a sample resulting from a clarified plasmapheresis of a HCV infected patient to obtain a HCV enriched pellet;
- resuspension of the HCV enriched pellet in an aqueous solution;
- ultracentrifugation of the resuspended HCV enriched pellet in a sucrose density gradient to separate the elements of the resuspended HCV enriched pellet into fractions according to their density;
- recovery of the fractions containing from about $5.10^5$ to about $10^6$ UI of HCV RNA per ml, from about 50 to about 100 pg of HCV core protein per ml, and containing particles capable of binding to the monoclonal antibody defined above as D32.10 or D4.12.9, to obtain a composition of purified HCV enveloped complete viral particles.

The selection step can proceed as described above.

According to another embodiment, the invention relates to a process for preparing a monoclonal antibody directed against HCV, in particular HCV enveloped subviral particles, comprising the following steps:
- immunizing an animal, in particular a mammal, with a composition of HCV enveloped subviral particles of the invention, or prepared according to the invention, and recovering the generated antibodies;
- selecting, among the generated antibodies, monoclonal antibodies on their ability of binding to the HCV enveloped subviral particles contained in the above mentioned composition of HCV enveloped subviral particles.

The composition of HCV enveloped subviral particles can be obtained as follows:
- at least two ultracentrifugations of a sample resulting from a clarified plasmapheresis of a HCV infected patient to obtain a HCV enriched pellet;
- resuspension of the HCV enriched pellet in an aqueous solution;
- ultracentrifugation of the resuspended HCV enriched pellet in a sucrose density gradient to separate the elements of the resuspended HCV enriched pellet into fractions according to their density;
- recovery of the fractions containing substantially no HCV RNA, substantially no HCV core protein and containing particles capable of binding to the monoclonal antibody defined above as D32.10 or D4.12.9, to obtain a composition of HCV enveloped subviral particles.

The selection step can proceed as described above.

The present invention more particularly relates to antibodies directed against the HCV enveloped subviral particles of the invention.

The invention also relates to a pharmaceutical composition comprising as active substance at least one antibody directed against HCV enveloped subviral particles and a pharmaceutically acceptable vehicle.

According to another embodiment, the invention relates to a pharmaceutical composition comprising as active substance the HCV enveloped subviral particles as defined above, or the composition comprising the HCV enveloped subviral particles as defined above, and a pharmaceutically acceptable vehicle.

Additionally adjuvants, such as defined for instance in Remington's Pharmaceutical Sciences $16^{th}$ ed./Mack Publishing Co. can be added to the pharmaceutical composition, adjuvants may be for instance incomplete Freund's adjuvant, aluminum salts or aluminum hydroxide.

The composition can be administrated, for instance, in a single dose comprising from 1 mg to 1 g of HCV enveloped subviral particles.

According to another embodiment, the invention relates to the use of the HCV enveloped subviral particles as defined above, or of the composition comprising the HCV enveloped subviral particles as defined above, to induce an immune reaction against said HCV enveloped subviral particles or against HCV enveloped complete viral particles as defined above.

The expression "induce an immune reaction" means that B cells secreting antibodies directed against HCV viral particles can be activated or that T cells destroying cells infected by HCV can be activated.

According to another embodiment, the invention relates to the use of the HCV enveloped subviral particles as defined above, or of the composition comprising HCV enveloped subviral particles defined above, for the preparation of a medicament for the diagnostic, the prevention or the treatment of HCV infections.

The HCV enveloped subviral particles can be used to assess the presence of antibodies directed against HCV in immunoassays according to method well known to the man skilled in the art, such as EIA, ELISA.

The HCV enveloped subviral particles can be used for the preparation of a vaccine against hepatitis C, in particular a therapeutic vaccine.

The expression "therapeutic vaccine" means that the vaccine is capable of improving the condition of patient infected by HCV, for example by inducing the production of antibodies directed against HCV.

BRIEF DESCRIPTION OF THE DRAWINGS

FIGS. 1A, 1B, 1C, 1D and 1E represent sodium dodecyl sulfate-polyacrylamid gel electrophoresis (SDS-PAGE) of antibody precipitated lysates of $^{35}$S labeled cells. Lanes 1, 2, 3, 4, 5, 6 and 7 correspond respectively to antibodies C9.19.16, C2.22.1, D32.10, D3.20.12, C7.24.19, C7.14.41 and C1.9.3. MW corresponds to a molecular weight marker. The size of the bands corresponding to the molecular weight marker, are presented on the right of the gel. When possible the bands are identified on the left of the gel as E1, E2 or Agg (for aggregated).

FIG. 1A represents a SDS-PAGE of antibody precipitated lysates of $^{35}$S labelled control cells, in reducing conditions.

FIG. 1B represents a SDS-PAGE of antibody precipitated lysates of $^{35}$S labelled cells expressing HCV E1 protein, in reducing conditions.

FIG. 1C represents a SDS-PAGE of antibody precipitated lysates of $^{35}$S labelled cells expressing HCV E2 protein, in reducing conditions.

FIG. 1D represents a SDS-PAGE of antibody precipitated lysates of $^{35}$S labelled cells expressing HCV E1E2 protein, in reducing conditions.

FIG. 1E represents a SDS-PAGE of antibody precipitated lysates of $^{35}$S labelled cells expressing HCV E1E2 protein, in non-reducing conditions

FIG. 2 represents the Western blotting of HCV viral particles, using D32.10 monoclonal antibody, under non-reducing and reducing conditions. From left to right, M represents a molecular weight marker, under non-reducing conditions, the size of its bands being indicated on the left of the gel (in kDa), lane 1 represents the Western blotting of HCV viral particles, using D32.10 monoclonal antibody, under non-reducing conditions, second lane M represents a molecular weight marker, under reducing conditions, lane 2 represents the Western blotting of 2.5 µg of HCV viral particles, using D32.10 monoclonal antibody, under reducing conditions, lane 3 represents the Western blotting of 5 µg of HCV viral particles, using D32.10 monoclonal antibody, under reducing conditions. On the right of the gel, the size of several bands of lane 3 are indicated (in kDa), some corresponding to HCV protein E2 (60 and 68) or to HCV protein E1 (34 and 31).

FIGS. 3A and 3B represent the Western blotting of HCV viral particles submitted to deglycosylation by glycosidase A (FIG. 3A) and by endoglycosidase H (FIG. 3B).

In FIG. 3A, lane M represents a molecular weight marker, the size of three of its bands being indicated (in kDa) on the left of the gel; lane 1, 2, 3 and 4 represent respectively glycosidase concentrations of 20, 10, 5 and 0 mU/ml. On the right of the gel, the positions of HCV proteins E2 and E1 are indicated, as well as the position of a major deglycosylated form of protein E1 (E1*) and the size (in kDa) of several bands corresponding to deglycosylated forms of E1 or E2, as well as the major deglycosylated form of E2 (41*).

In FIG. 3B, lane M represents a molecular weight marker, the size of four of its bands being indicated (in kDa) on the left of the gel; lane 1 and 2 represent respectively a control deglycosylation experiment carried out without endoglycosidase H and a deglycosylation experiment carried out in presence of endoglycosidase H. On the right of the gel are represented the major bands corresponding to the fully glycosylated forms of E2 and E1 and to deglycosylated forms of E2 (50, 48, 46 and 42 kDa) and E1 (28 and 24 kDA). The predominant deglycosylated forms of E2 (50*) and E1 (28*) are marked by a star.

FIG. 4 represents the characterization of the fractions obtained by centrifugation on a sucrose density gradient of a HCV viral particles preparation. Three parameters have been measured, HCV RNA content, HCV core protein content and reactivity towards D32.10 monoclonal antibody. The horizontal axis represents the numbers of the fractions submitted to characterization. The left vertical axis represents HCV RNA concentration ($\times 10^5$ UI/ml) and a measure of the reactivity towards D32.10 as measured by indirect EIA (OD at 450 nm). The right vertical axis represents the HCV core protein concentration (in pg/ml). The curve corresponding to the black dots represents the reactivity of the fractions towards D32.10, the curve corresponding to the white triangles represents the fractions contents in core protein and the dotted bars represent the fractions contents in HCV RNA.

FIGS. 5A, 5B and 5C represent respectively transmission electron microscopy pictures of a HCV viral particles preparation, of a HCV enveloped complete viral particles preparation and of a HCV enveloped subviral particles preparation.

In FIG. 5A, the horizontal bar represents a scale of 200 nm in length. The larger circular elements represent HCV enveloped complete viral particles and the smaller circular elements represent HCV enveloped subviral particles.

In FIG. 5B, the horizontal bar represents a scale of 50 nm in length. The circular elements represent HCV enveloped complete viral particles.

In FIG. 5C, the horizontal bar represents a scale of 50 nm in length. The circular elements represent HCV enveloped subviral particles.

FIG. 6 represents the Western blotting of HCV viral particles, using D4.12.9 monoclonal antibody. Lanes M represent a molecular weight marker, the size of four of its bands (75, 50, 37, 25) being indicated (in kDa) on the left side and on the right side of the gel. Lanes 1 and 2 represent the result of a digestion of the HCV viral particles by glycosidase A and by endoglycosidase H respectively, lanes 3 and 4 represent the result of a proteolytic digestion of HCV viral particles by proteases trypsin and V8, lane 5 represents the result of lysis by NP-40, and in lane 6 no prior treatment as been performed. On the right of the gel, the two major forms of undigested E2 protein (68 and 48) are indicated (in kDa), and on the left of the gel the major deglycosylated form of E2 (E2*) is represented.

FIG. 7 represents a D4.12.9 based characterization of fractions obtained by centrifugation on a sucrose density gradient of a HCV viral particles preparation. In addition to the fractions reactivity towards D4.12.9, the fractions contents in core protein was also measured. The horizontal axis represents the numbers of the fractions submitted to characterization. The right vertical axis represents a measure of the reactivity towards D4.12.9 as measured by indirect EIA (OD at 450 nm). The left vertical axis represents the HCV core protein concentration (in pg/ml). The curve corresponding to the black squares represents the reactivity of the fractions towards D4.12.9, the curve corresponding to the black diamond shapes represents the fractions contents in core protein.

FIGS. 8A, 8B and 8C represent the immunoreactivity of three biotinylated peptides, comprising respectively amino acids 290-317 (FIG. 8A), amino acids 471-500 (FIG. 8B) and amino acids 605-629 (FIG. 8C), towards 55 sera of healthy individuals (11 sera, numbered T1 to T11 on the horizontal axis) and HCV infected patients (44 sera, numbered A1 to A44 on the horizontal axis). The vertical axis represents the reactivity of the sera to the three peptides as measured by ELISA (OD at 492 nm ×1000). The white bars represent the reactivity of the healthy individuals' sera and the grey bars represent the reactivity of the infected patients' sera. The horizontal line represents a cut-off value above which a serum response is considered positive. In FIG. 8A, the cut-off value is 0.691, in FIG. 8B, 0.572 and in FIG. 8C, 0.321.

HCV core protein was quantified by the Total HCV core antigen assay from Ortho Clinical Diagnostics (FIG. 9A) and analyzed by Western blotting (FIG. 9B) in HCV-Fan pellet and the fractions from 30 to 45% sucrose gradient of type 1 described above. (FIG. 9A) All the fractions were tested at a dilution of 1:2. HCV-Fan pellet was tested at dilutions 1:25, 1:50 and 1:100, and found to contain 332 pg/ml. All dilutions were made with TNE buffer. The cutoff value was 1.4 pg/ml. (FIG. 9B) HCV-Fan pellet and fractions 4, 8, 12 and 13 from the 30-45% sucrose gradient were subjected to SDS-12.5% PAGE. HCV core proteins were detected using a mixture of monoclonal antibodies anti-core, 7G12A8, 2G9A7 and 19D9D6 (5 µg/ml for each). The blots were developed using the ECL Plus system from Amersham. Numbers on the left indicate molecular weights of markers (M) in kilodaltons (kDa), and the HCV core proteins were indicated on the right.

HCV RNA was analyzed by the quantitative RT-PCR Amplicor HCV Monitor test version 2.0 (Roche Diagnostics) in all the fractions from the initial 10 to 60% sucrose gradient. The test was performed according to the manufacturer's instructions. The results were calculated by using the QS International Units (IU) per PCR, which was specific for each lot, and expressed in IU HCV RNA/ml.

Figure 11A:
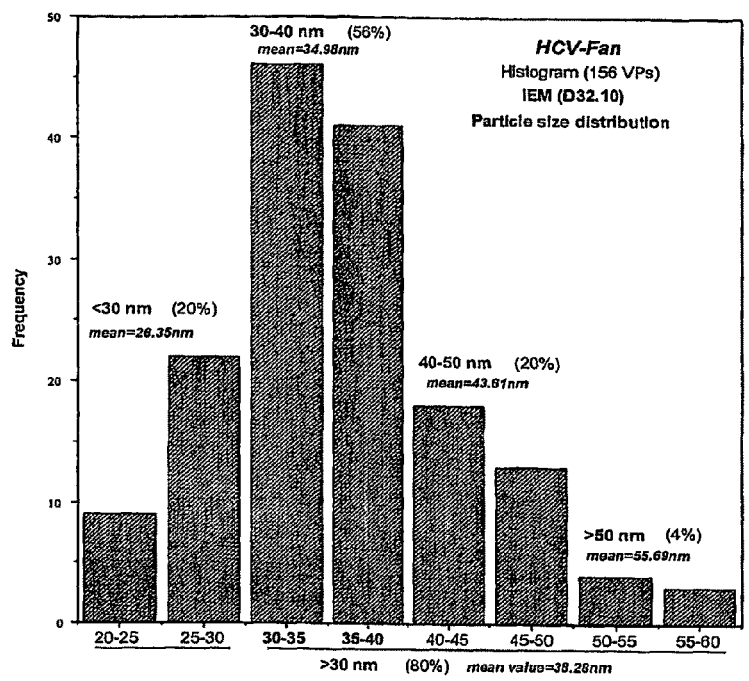
Figure 11B:
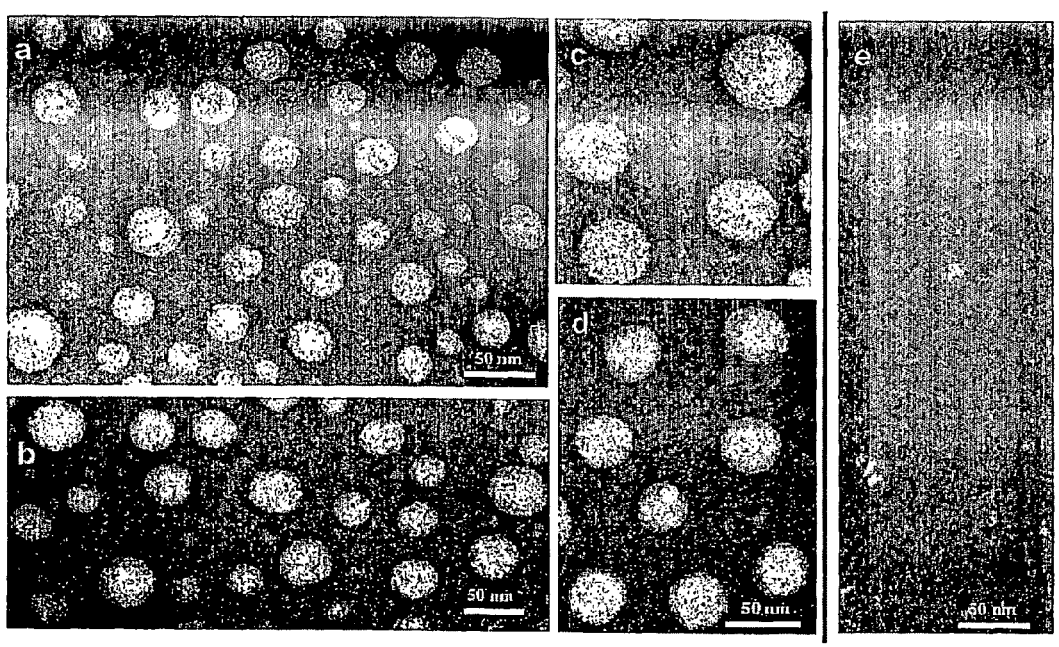

FIG. 11A and FIG. 11B

Analysis of serum-derived HCV enveloped particles by electron microscopy (EM). HCV-Fan pellet (2 µg) was immunoprecipitated by using MAb D32.10 (5 µg) (panels a, b, c and d) or irrelevant MAb (panel e), and the immune-complexes after pelleting by ultracentrifugation were absorbed onto grids and stained with 1% uranyl acetate (pH 4.5). The preparations were visualized using a JEOL 100 CX electron microscope. (FIG. 11A) The particles vary somewhat in diameter (expressed in nm), and histogram was performed on 156 viral particles (VPs). Particle size distribution shows a peak centered at 35 nm. (FIG. 1B) Electron micrographs. Bars in panels a, b, c, and e indicate 50 nm.

Figure 12A:
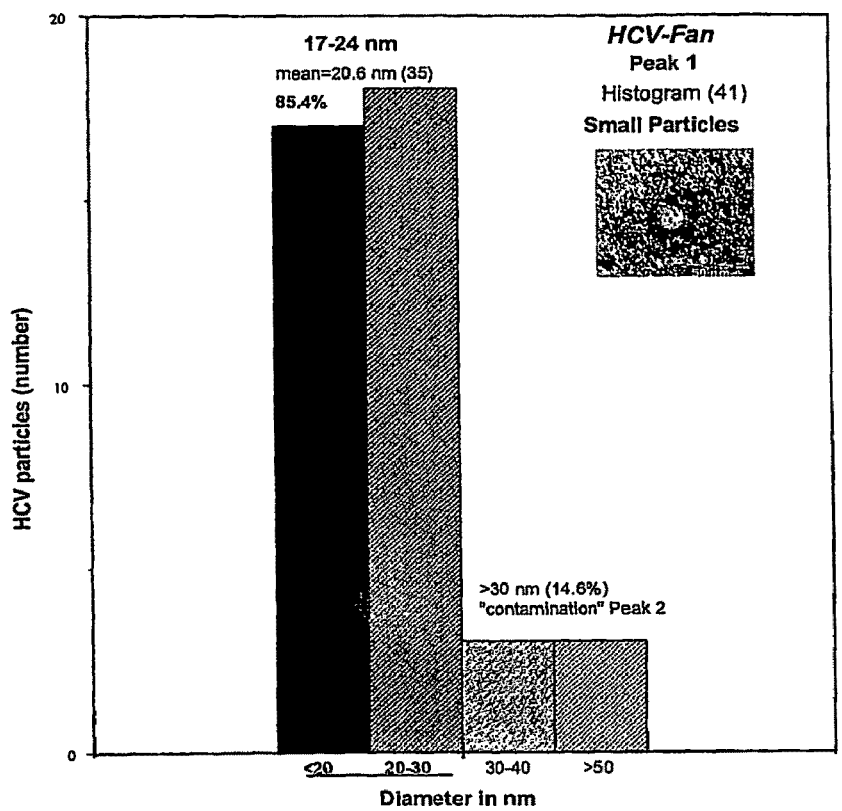
Figure 12B:
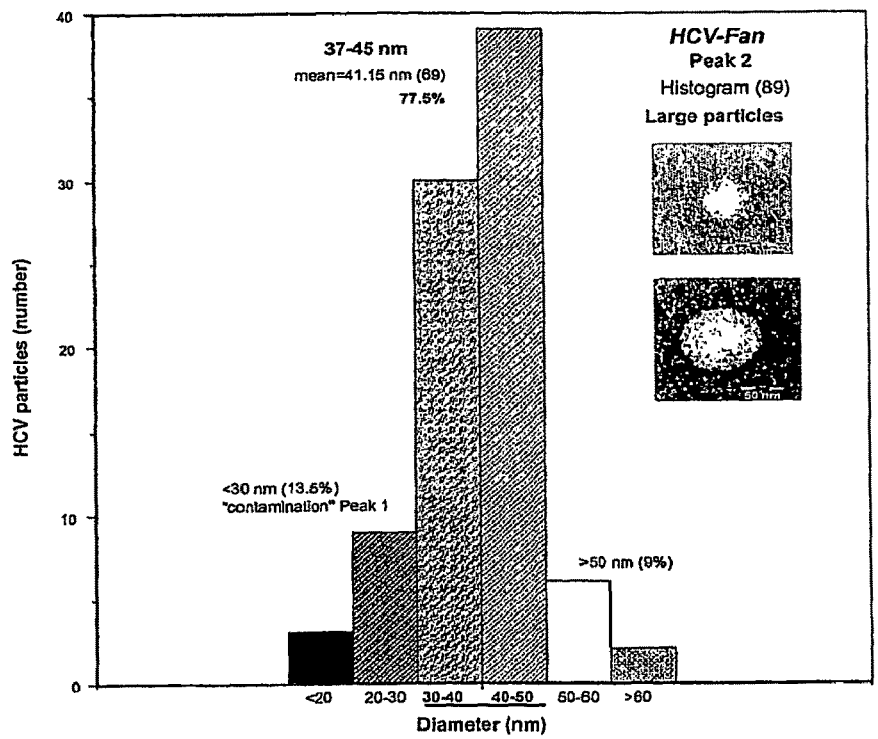

FIG. 12A and FIG. 12B

Analysis by electron microscopy of HCV-Fan particles from sucrose gradient peaks 1 (FIG. 12A) and 2 (FIG. 12B) after immunoprecipitation by D32.10, adsorption on grids and staining. (FIG. 12A) Histogram was performed on 41 viral particles. The predominant species (85.4%) in peak 1 was a spherical particle with a diameter of about 20 nm, so-called <<small particles>>. (FIG. 12B) Histogram was performed on 89 viral particles. The most prevalent forms (77.5%) in peak 2 had a mean diameter of about 41 nm. Peak 2 appeared somewhat more heterogeneous in size, and consisted primarily of 35 and 50-nm-diameter particles, so-called <<large particles>>. Bars, 50 nm.

FIG. 13

Indirect immuno-gold labeling of enveloped HCV particles. The microscope grids coated with the D32-10-immune complexes (HCV pellet, 20 µg; MAb D32.10, 5 µg) were incubated with a 1:50 dilution of goat anti-mouse IgG-conjugated colloidal gold particles (10 nm), as second antibody. According to steric hindrance of IgG (about 15 nm in EM), only few gold-particles could identify antibody binding. No gold-particles were observed outside the viral particles. Bars in all panels indicate 20 nm.

FIG. 14A, FIG. 14B, FIG. 14C and FIG. 14D

Figure 14A:
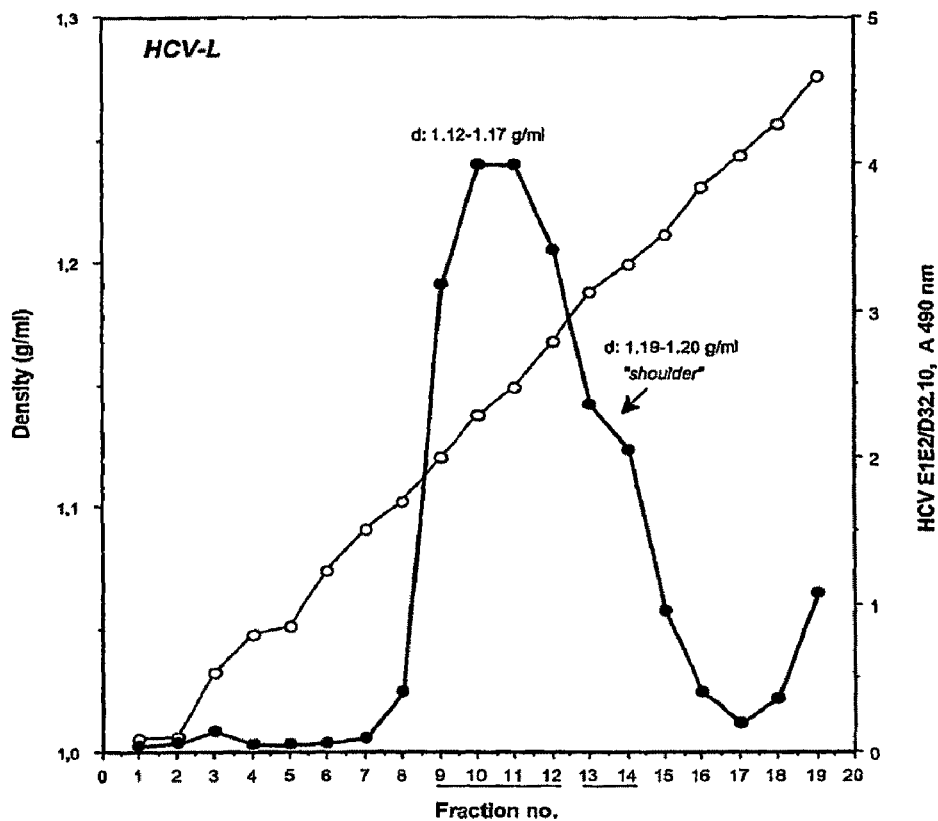
Figure 14B:
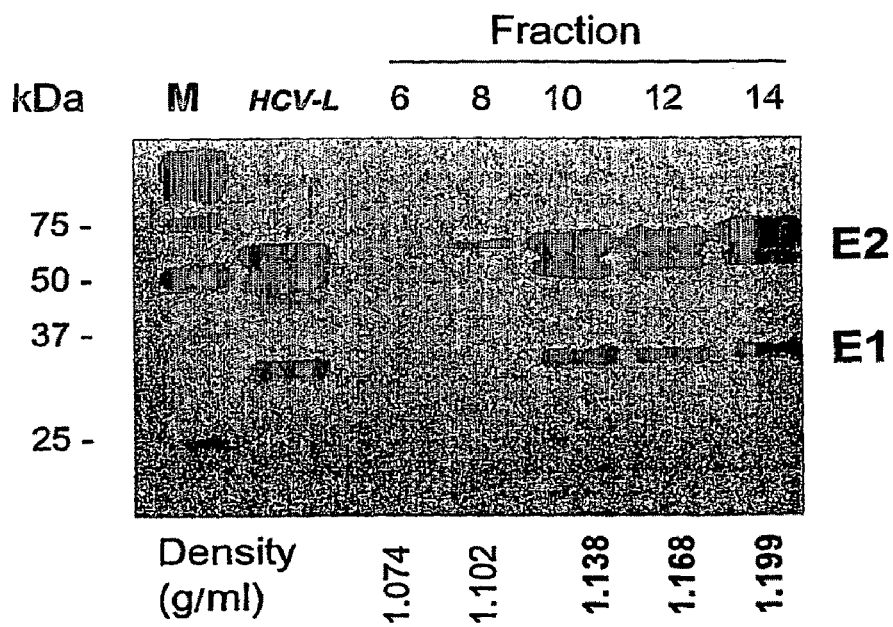

FIGS. 14A and 14B represent the result of the isopycnic centrifugation in sucrose density gradient (10% to 60%) of HCV-enriched pellets from the isolate HCV-L of genotype 1b.

FIG. 14A represents the density (left horizontal axis, g/ml) and the E1E2-D32.10 reactivity (right vertical axis, $A_{490\,nm}$) of the fractions (horizontal axis) obtained after centrifugation.

FIG. 14B represents the Western blotting of fractions 6, 8, 10, 12 and 14, using the anti-E1E2 MAb D32.10. Numbers on the left indicate molecular weights of markers (M) in kilodaltons (kDa), and the HCV E1 and E2 proteins were indicated on the right.

Figure 14C:
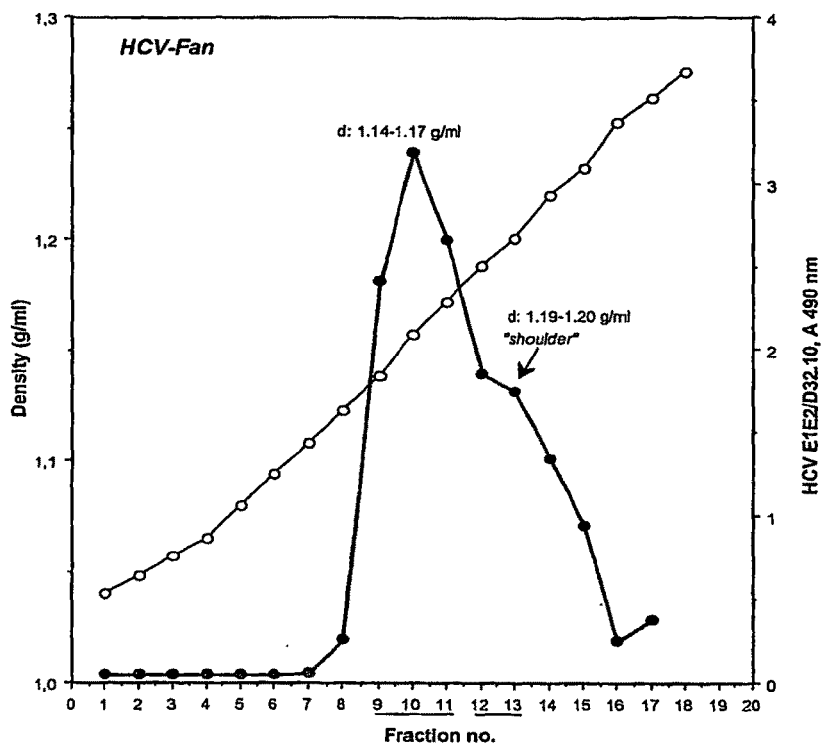
Figure 14D:
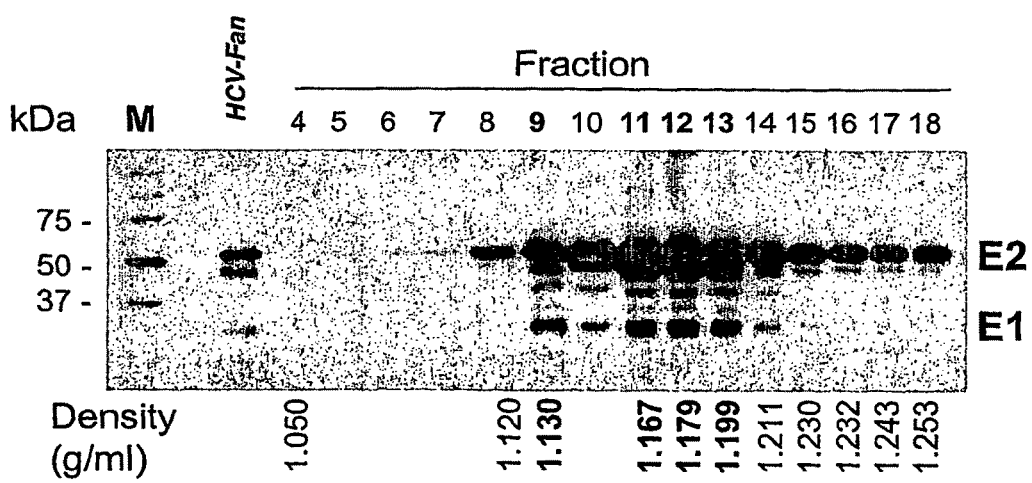

FIGS. 14C and 14D represent the result of the isopycnic centrifugation in sucrose density gradient (10% to 60%) of HCV-enriched pellets from the isolate HCV-Fan of genotype 1a/2a.

FIG. 14C represents the density (left horizontal axis, g/ml) and the E1E2-D32.10 reactivity (right vertical axis, $A_{490\,nm}$) of the fractions (horizontal axis) obtained after centrifugation.

FIG. 14D represents the Western blotting of fractions 6, 8, 10, 12 and 14, using the anti-E1E2 MAb D32.10.

For EIA, each fraction was diluted at 1/10000 (FIGS. 4A and 4C), and for Western blotting 5 µl upper lane of the selected fractions was used (FIGS. 4B and 4D). The density of fractions was determined by refractometry and expressed in g/ml. Absorbance (A) was determined at 490 nm. The results of EIA were considered as positive when superior to cut-off, corresponding to mean of negative controls (at least three values) multiplied by 2.1. The blots were developed using the ECL Plus system from Amersham.

Figure 15A:
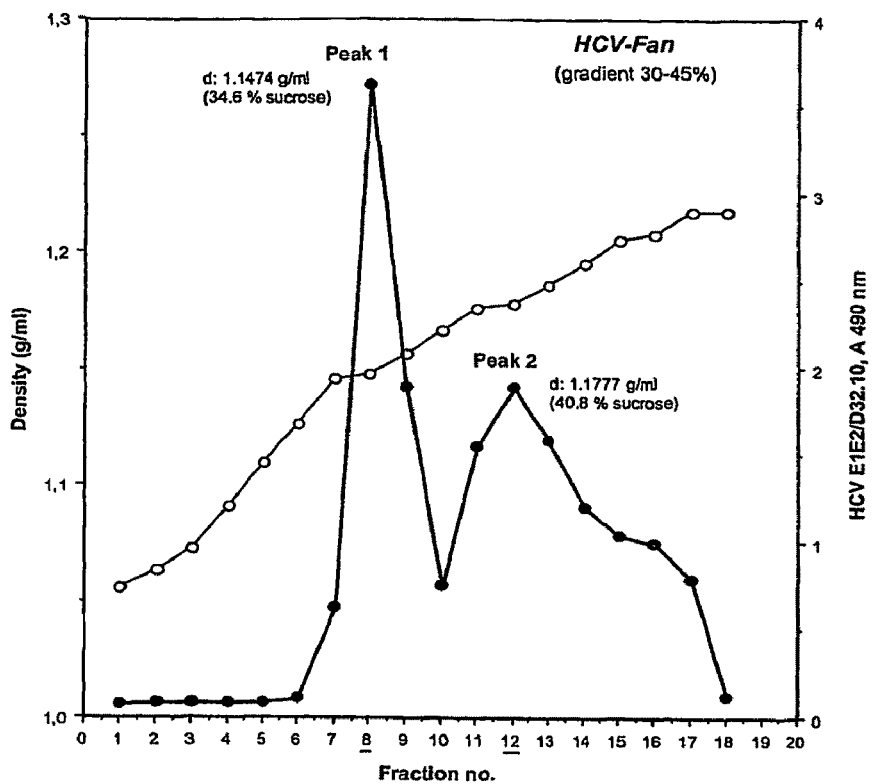
Figure 15B:
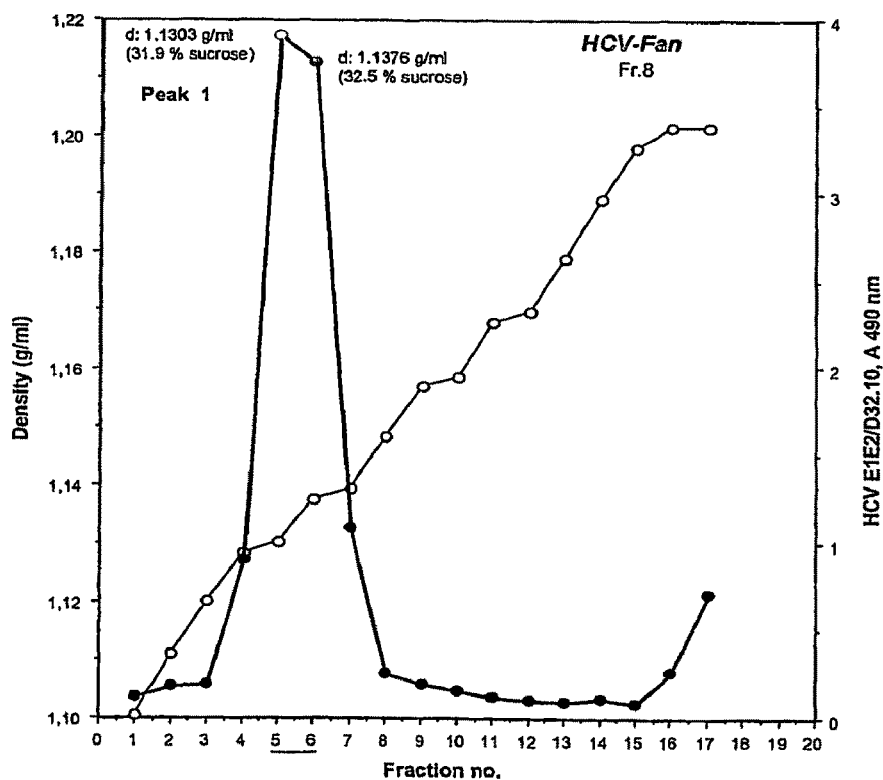
Figure 15C:
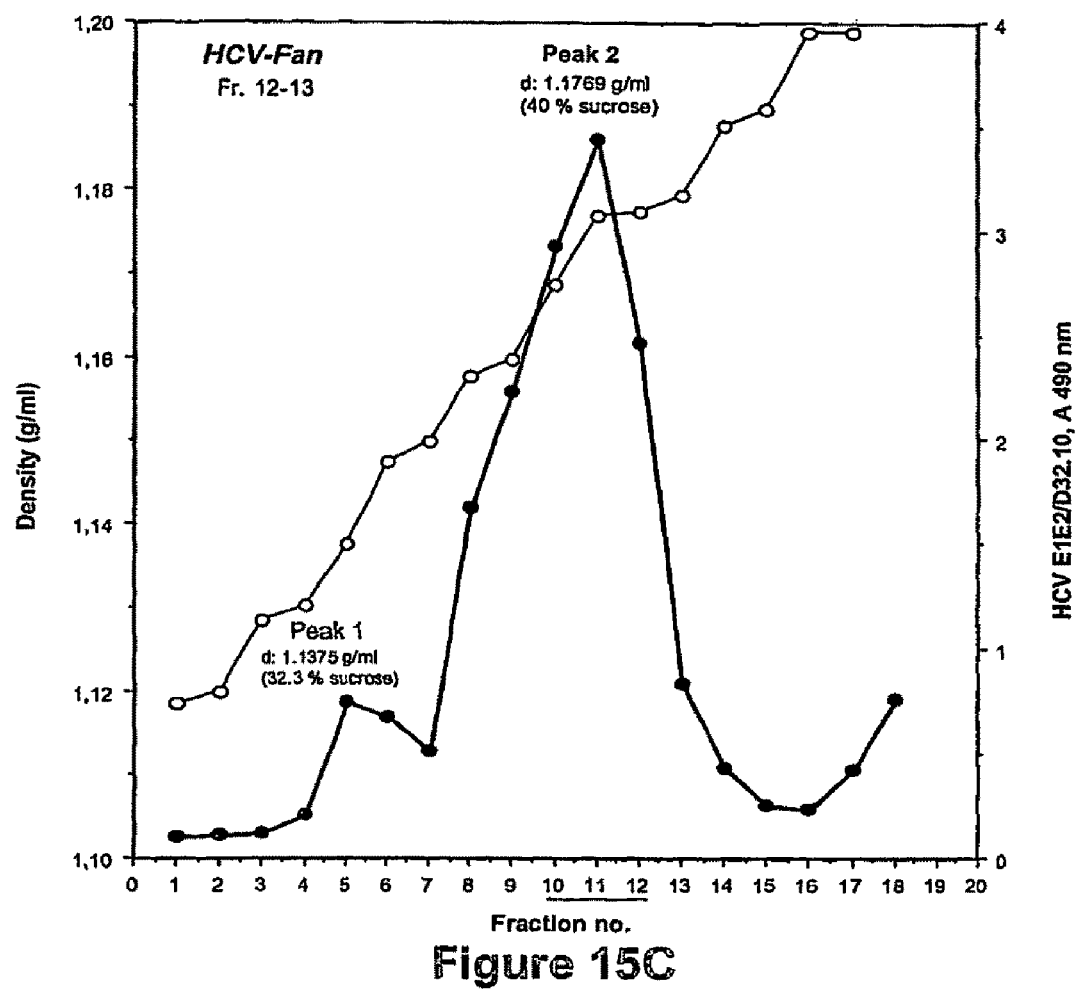

FIG. 15A, FIG. 15B and FIG. 15C

Isopycnic centrifugation in a 30 to 45% sucrose gradient of type 1 (2 ml of 30%, 3 ml of 35%, 3 ml of 40%, 2 ml of 45%) of the HCV-Fan pellet (FIG. 15A). Particles from sucrose gradient (30-45%) peaks 1 (fraction 8) and 2 (fractions 12 and 13) were subjected individually to a second equilibrium centrifugation (FIGS. 15B and 15C, respectively). Peak 1 was centrifuged in a 30 to 45% sucrose gradient of type 2 (3 ml of 30%, 3 ml of 35%, 2 ml of 40%, 2 ml of 45%) (FIG. 15B). Peak 2 was centrifuged in a 30 to 45% sucrose gradient of type 3 (2 ml of 30%, 2 ml of 35%, 3 ml of 40%, 3 ml of 45%) (FIG. 15C). The density of fractions determined by refractometry was expressed in g/ml. E1E2-D32.10 reactivity was analyzed by indirect EIA, as previously.

DETAILED DESCRIPTION OF THE PREFERRED EMBODIMENTS

EXAMPLE 1

Obtaining a Monoclonal Antibody Directed Against the Natural HCV Viral Envelope

HCV Viral Particles Preparation

To obtain virus materials in good supply, the purification of HCV viral particles was performed from plasmaphereses.

The selected patient developed chronic active hepatitis C after partial liver transplantation for C viral cirrhosis, and 12-months later multiple myeloma associated with hypergammaglobulinemia which was the cause of plasma exchange. The patient showed abnormal elevated serum aminotransferase (ALT/AST) levels and was positive for anti-HCV antibodies. The patient was negative for all HBV and HIV markers. The HCV RNA content of initial material was $6 \times 10^5$ copies/ml (Amplicor™ HCV Monitor™, Roche Diagnostics, Meylan, France), and the genotype 1b (INNO-LIPA assay, Innogenetics, Gent, Belgium).

Clarified plasmapheresis was used to prepare a HCV-enriched pellet by two successive ultracentrifugations at 210,000 g for 4 h at 4° C. The final pellet was resuspended in 1 ml of Tris-NaCl-EDTA (TNE) buffer (20 mmol/L Tris-HCl, pH 7.5, 100 mmol/L NaCl, 1 mmol/L EDTA) (concentration 240 fold), and stored at −80° C. The HCV RNA content of this material was $3 \times 10^7$ copies/ml (Monitor, Roche) and the protein concentration 5 mg/ml (i.e. about $10^7$ copies of HCV RNA per mg of protein).

Hybridoma Preparation

For generation of monoclonal antibodies (mAbs), BALB/c mice were inoculated with 100 µg ($10^6$ copies of HCV RNA) of HCV-pelleted material in complete Freund adjuvant, followed 1 week later with 100 µg of virus in incomplete Freund adjuvant. The three immunized mice developed high serum antibody titers against HCV, detected by indirect enzyme immunoassay (EIA). Three weeks later, mice were boosted with 50 µg of virus in phosphate buffered saline (PBS). After 5 days the injection was repeated and 3 days later the spleen was removed for fusion with X63 myeloma cells by the procedure described by Buttin et al. (1978). Hybridoma culture supernatants were screened for the presence of HCV-specific antibodies by indirect EIA using the immunogen as the solid phase (5 µg/ml) and peroxidase-conjugated F(ab')2 fragment of anti-mouse immunoglobulins (Amersham, France) as a revelation secondary antibody (Petit et al., 1987). The diluent contained 50% normal human serum (NHS) to eliminate non-specific reactivity directed against NHS proteins possibly associated with HCV viral particles. The hybrids giving the strongest signal (P/N>10) to HCV were then recloned by limiting dilution and their specificity further determined. Seven clones (C9.19.16, C2.22.1, D32.10, D3.20.12, C7.24.19, C7.14.41 and C1.9.3) were selected and four (D32.10, C2.22.1, C9.19.16 and D3.20.12) were propagated by injection into pristane-primed BALB/c mice for ascitic fluid production, and then purified by precipitation with 50% saturated $(NH_4)_2SO_4$ followed by affinity chromatography in Sepharose-Protein G (Pharmacia, France). Isotype was determined by ELISA with methods well known to the man skilled in the art. The seven clones analyzed gave antibodies of the IgG1 isotype.

Monoclonal Antibody Characterization

Indirect EIA was used to evaluate the interaction of the above mentioned monoclonal antibodies with the viral particles. Polystyrene plates of 96-wells (Falcon; Becton Dickinson France S. A, Le Pont de Claix) were coated with the HCV preparation (1 mg of protein per ml) diluted from $10^{-1}$ to $10^{-6}$ (corresponding to 100 µg/ml to 1 ng/ml). The plates were incubated overnight at 4° C. and were then saturated with Tris-NaCl (TN) buffer (20 mM Tris-HCl, pH 7.5 and 100 mM NaCl) containing 5% (w/v) bovine serum albumin (BSA). mAb D32.10 diluted in a mixture of TN/BSA buffer and 50% normal human serum (NHS) at a concentration of 5 µg/ml was added to each well and incubated for 2 h at 37° C. The bound antibody was detected with the horseradish peroxidase (HRPO)-conjugated F(ab')2 fragment of anti-mouse immunoglobulins (diluted 1/5,000; Immunotech) and with orthophenylenediamine (OPD) and hydrogen peroxide ($H_2O_2$) as substrates. Optical density (OD) was determined at 450 nm with an ELISA plate reader (MRX, Dynex). The results were considered as positive when superior to cut-off, corresponding to mean of negative controls multiplied by 2.1. The seven antibodies obtained did recognize the viral particles.

To establish the native polypeptide specificity of the mAbs, immunoblotting using the immunogen as antigenic probes (Petit et al., 1987) was carried out. Sodium dodecyl sulfate (SDS)-polyacrylamide gel electrophoresis (PAGE) on 12.5% gels was performed under reducing conditions (2% SDS+5% 2-ME). After protein transfer onto PVDF membranes, mAbs (2 to 5 µg/ml) were tested as primary antibodies, diluted in 50% NHS, and IgGs bound were detected by incubation with peroxydase-conjugated (Fab')2 fragment of anti-mouse immunoglobulins (diluted 1/10,000: IMMUNOTECH), as secondary antibody. Bands were visualized by enhanced chemoluminescence (ECL+) system from Amersham.

All mAbs tested, except D32.10, gave negative reactions with HCV polypeptides under reducing conditions. It is worth noting that the mAbs selected were not reactive with either human serum albumin or with γ- or µ-chains of immunoglobulins (Ig), except C1.9.3 and C7.24.19 which faintly reacted with human IgG in EIA (approximately 5-fold the negative value).

Figure 1A:
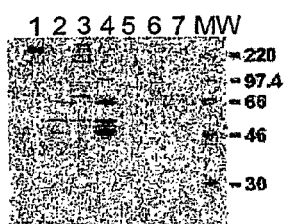
FIG. 1A, FIG. 1B, FIG. 1C, FIG. 1D and FIG. 1E
Figure 1B:
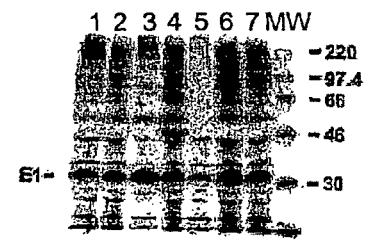
Figure 1C:
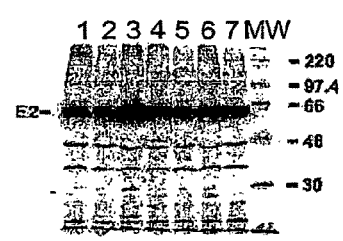
Figure 1D:
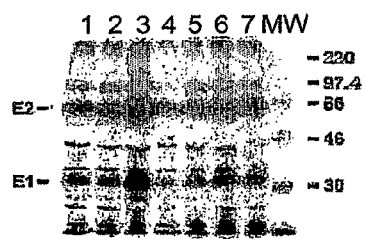
Figure 1E:
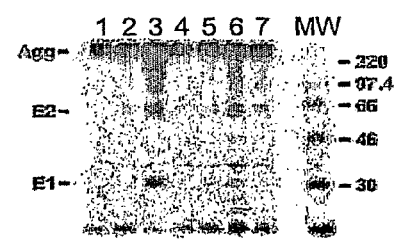

The polypeptide specificity of the seven antibodies was also examined by immunoprecipitation. HepG2 cells infected by vaccinia virus recombinants expressing HCV proteins (E1, E2 or E1E2) were metabolically labeled with $^{35}$S-Translabel (ICN) as previously described (Dubuisson et al., 1996). Cells were lysed with 0.5% NP-40 in 10 mM Tris-HCl (pH7.5), 150 mM NaCl, and 2 mM EDTA. The precipitates were treated with Laemmli sample buffer and analyzed by SDS-PAGE under reducing or non-reducing conditions (FIG. 1). The monoclonal antibodies tested did not show non specific reactivity directed against cellular components, except C9.19.16 (>200 kDa), D3.20.12 (three intense bands at 70, 50 and 46 kDa) and more faintly, C2.22.1 (70, 50, 46 kDa) and D32.10 (multiple very faint bands) (FIG. 1A, control vector). All antibodies specifically immunoprecipitated E1 (FIG. 1B) and E2 (FIG. 1C), when the two HCV glycoproteins were expressed separately, as well as E1E2 heterodimers (FIG. 1D), when these proteins were co-expressed. Interestingly, the pattern was different after SDS-PAGE under non-reducing and reducing conditions (FIG. 1D, 1E). All recognized disulfide-linked E1E2 aggregates, which were detected in the upper part of the gels under non-reducing conditions (FIG. 1E). One mAb, D32.10, was found to react mostly with aggregates and also with E1E2 non covalently-linked mature complex (FIG. 1E, non-reducing conditions). All mAbs did not recognize denatured recombinant E1 or E2 proteins expressed in heterologous system by Western blot analysis, suggesting they recognized conformational epitopes on HCV viral particles. Collectively, these results indicate that these mAbs specifically recognize disulfide-linked E1E2 complexes expressed at the surface of natural serum-derived HCV viral particles. It is highly probable that they react with a shared conformational epitope between E1 and E2 proteins. Monoclonal antibody D32.10, which interacts with the E1E2 complex under its covalent or non-covalent form was chosen for further studies.

Monoclonal Antibody D32.10 Antigen Mapping

To test the HCV type specificity of D32.10, an indirect EIA was carried out, according to the procedure already described, with four different HCV preparations (1 mg of protein per ml) diluted from $10^{-1}$ to $10^{-6}$ (corresponding to 100 µg/ml to 1 ng/ml). In addition to the immunogen HCV preparation, a preparation obtained from the same patient was used, as well as two other preparation obtained from two different patients with chronic hepatitis C, one of the patient having been found to carry to distinct genotypes in serum, namely HCV1a and HCV2a. D32.10 was found able to recognize all four of the HCV preparations, thereby indicating that it is able of recognizing determinants not restricted to the 1b genotype of the immunogen.

To assess the native polypeptide specificity of D32.10 a Western blot analysis was carried out. Untreated HCV-enriched pellet was used as the antigenic probe, at different concentrations, varying from 0.1 to 1 mg/ml. The antigen was subjected to sodium dodecyl sulfate-polyacrylamide gel electrophoresis (SDS-PAGE) on 12.5% gels under reducing or non-reducing conditions (2% SDS±5% 2-mercaptoethanol (2-ME)). After protein transfer onto PVDF membranes, immunoblotting was performed using mAb D32.10 (2 to 5 µg/ml) as primary antibody, diluted in 50% NHS. Mouse IgGs bound were then detected by incubation with peroxidase-conjugated (Fab')2 fragment of anti-mouse immunoglobulins (diluted 1/10,000; DAKO), as secondary antibody. Protein bands were visualized by enhanced chemiluminescence (ECL+) system from Amersham. Glycosidase digestion was performed as previously described by Sato et al. (1993) on circulating HCV virions. The HCV-enriched pellet (HCV-L, 4 µg) was treated with 5, 10 or 20 mU/ml of glycosidase A (peptide-N-glycosidase A or PNGase A; ROCHE) in 100 mM citrate/phosphate buffer (pH 6.0) for 18 h at 37° C. Deglycosylation of purified HCV viral particles was also performed by incubation overnight at 37° C. in 50 mM sodium acetate buffer (pH 5.5) containing endoglycosidase H (endo H, 5 mU/µl from Roche), 20 mM dithiothreitol (DTT) and 0.1% Triton X100. The control digestion was performed using the same conditions as for the PGNase A digestion or the endo H digestion, except that the enzyme was omitted. Samples were then treated with electrophoresis sample buffer containing reducing agent and analyzed by SDS-PAGE.

Figure 2:
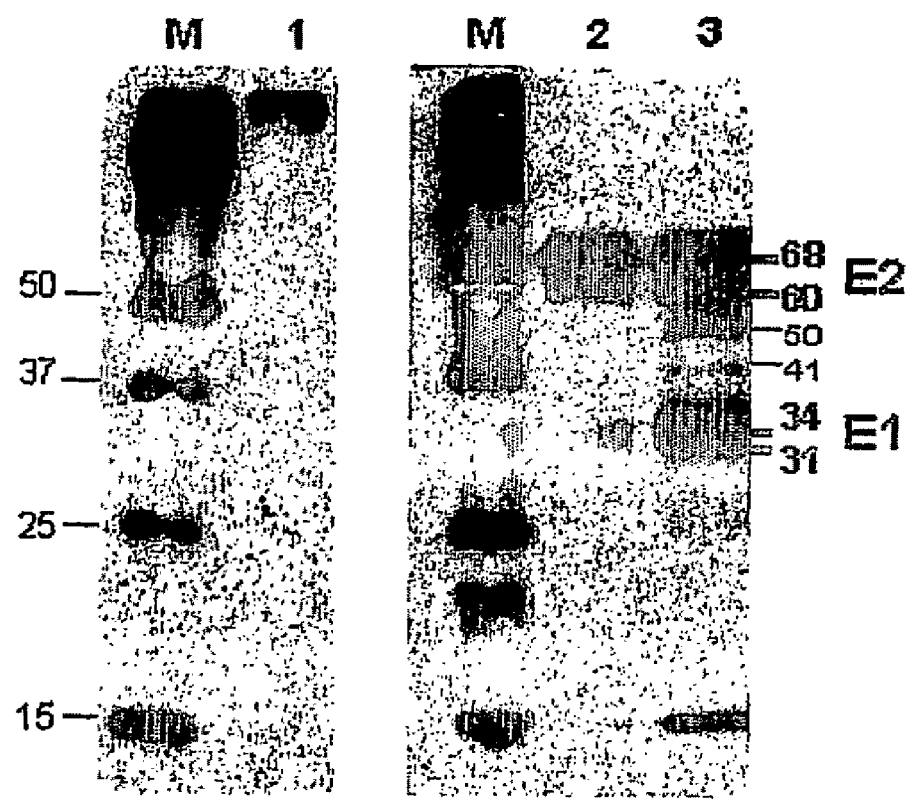
FIG. 2

The results of the Western blot experiment are presented in FIG. 2. When two concentrations of the same sample (2.5 and 5 µg, lanes 2 and 3, respectively) were analyzed under reducing conditions (2% SDS/5% 2-ME), mAb D32.10 recognized a major band of 68 kDa and another band of 31 kDa, corresponding to E2 and E1 respectively. However, under non-reducing conditions, mAb 32.10 recognized disulfide linked complexes recovered in the upper part of the gel (>200 kDa). These high molecular weight bands (FIG. 2, lane 1) very probably correspond to heterodimeric E1E2 complexes.

Figure 3A:
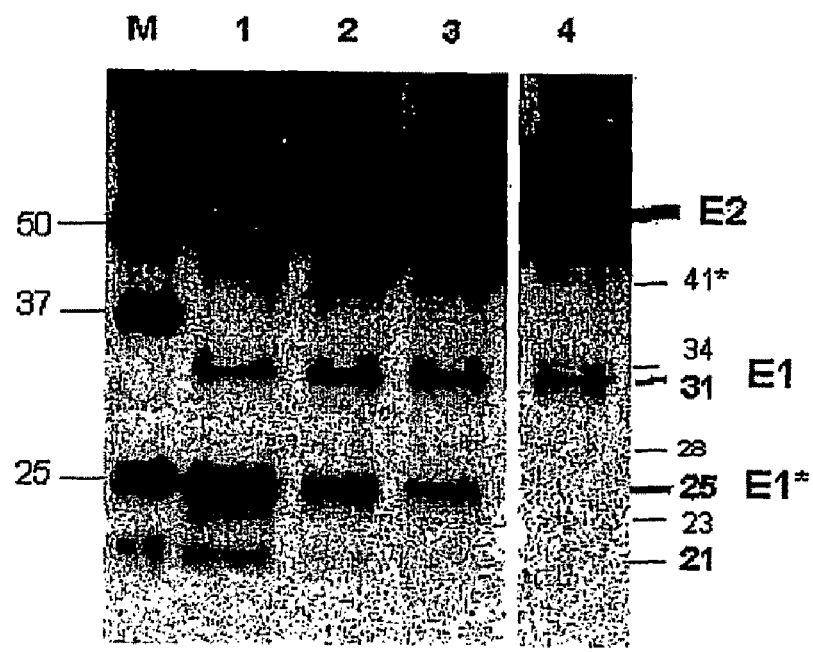
FIG. 3A and FIG. 3B
Figure 3B:
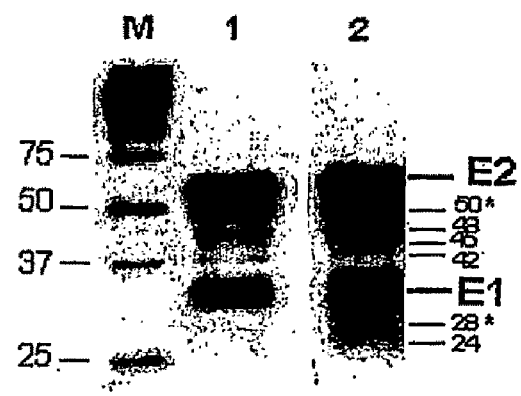

Asparagine-linked complex type sugar chains have been shown to be present on the surface of native virions of HCV (Sato et al., 1993), thus the ability of D32.10 mAb to recognize HCV-specific proteins after treatment of the HCV preparation with glycosidase (PNGase A) at different concentrations (20, 10 and 5 mU/ml) was examined. As shown in FIG. 3A (lanes 1, 2 and 3, respectively), D32.10 reacted with deglycosylated forms of E1, especially the 25 kDa species, which accumulated at the highest concentration of the enzyme. While E1-related products could be clearly detected by D32.10 after deglycosylation, the E2-related products were not clearly identified after the treatment. Endoglycosidase H (endo H) digestion allowed the investigation of the sensitivity of E1E2 complexes expressed on natural HCV viral particles to endo H cleavage. As shown in FIG. 3B, a shift in molecular weight was observed for both E2 (from 68 to 42 kDa) and E1 (from 34 to 24 kDa) proteins suggesting that E1 and E2 possess a complex glycosylation on serum-derived native HCV viral particles, accounting for partial endo H resistance, such as a mixture of endo H resistant complex glycans and sensitive forms.

D32.10 Epitope Mapping a. Screening of a Peptide Library

To further characterize the epitope recognized by mAb D32.10, the antibody was used to screen a dodecapeptide phage display library.

A Ph.D.-12™ Phage Display Peptide Library Kit was obtained from New England BioLabs Inc. This is a combinatorial peptide 12-mers fused to the minor coat protein (pIII) of M13 phage. The displayed peptide 12-mers are expressed at the N-terminus of pIII. The library consists of about $1.9 \times 10^9$ electroporated sequences, amplified once to yield about 20 copies of each sequence in 10 µl of the supplied phage. Three biopannings were performed according to the instruction of the manufacturer with some modifications. Briefly, 10 µg of biotinylated mAb D32.10 were coupled to 35 mm polystyrene Petri dish (Falcon) coated with 40 µg of streptavidin. The dish was incubated overnight at 4° C. and washed six times with 50 mM Tris, 150 mM NaCl, pH 7.5 (TBS) containing 0.5% Tween-20 (TBS-T). In the first round of selection, $4 \times 10^{10}$ phages from the initial library were allowed to react with the dish bound IgG for 4 h at 4° C. under rocking condition. The unbound phages were removed by repetitive washes with TBS-T. The bound phages were then eluted from the dish with 400 µl of elution buffer (0.1 N HCl, pH adjusted to 2.2 with glycine, 1 mg/ml BSA). After neutralisation with 75 µl of 1 M Tris-HCl pH 9.1, the eluted phages were then amplified by infecting 20 ml of a 1:100 dilution of an overnight culture of E. coli ER2537 (recA+strain cells), as recommended in the instruction manual. The culture was incubated for 4.5 h at 37° C. with vigorous shaking. The supernatants were obtained and precipitated with polyethyleneglycol (PEG) as previously described (Scott et al., 1990). In the second and third rounds of selection, 20% of the amplified phages from the preceding round were preincubated overnight at 4° C. with the biotinylated mAb D32.10 at the final concentration of 10 and 1 nM, respectively, before being added to the 35-mm polystyrene Petri dish coated with 10 µg of streptavidin. The procedure was then identical to the first round. The phages from the third biopanning eluate were then cloned and amplified for DNA sequencing and immunoanalysis.

For DNA sequencing, single-stranded DNA was prepared from the purified phages as described by Sambrook et al. (1982). The nucleotide sequence of the gene III inserts was determined according to the modified method of Sanger (Sanger et al., 1977) with an Applied Biosystems DNA sequencer (Model 377A) using the BigDye™ Terminator Cycle Sequencing Ready Reaction kit (Perkin-Elmer). Cycle sequencing was performed with a primer 5' HO-CCCTCAT-AGTTAGCGTAACG-OH 3' (SEQ ID NO: 4) corresponding to the pIII gene sequence. The aminoacid sequence of the insert was deduced from the nucleotide sequence.

For ELISA on supernatant phages, rows of ELISA plate wells were coated with 100 µl of either mAb D32.10 or an irrelevant mAb at the final concentration of 100 µg/ml in 0.1 M NaHCO$_3$ buffer (pH 8.6). The plates were incubated overnight at 4° C. and then were blocked with 0.1 M NaHCO$_3$ buffer (pH 8.6) containing 5 mg/ml of BSA. After 2 h incubation at 4° C. the plates were washed six times with TBS containing 0.5% Tween. Four fold serial dilutions of each phage clone were added to each well of the microtiter plate in a final volume of 100 µl of TBS-T, starting with $10^{12}$ virions in the first well of a row and ending with $2\times10^5$ virions in the 12th well. The plates were incubated for 2 h at room temperature with agitation and were then washed six times with TBS-T as above. The bound phages were detected in a sandwich assay using a horseradish peroxydase-conjugated anti-M13 mAb at a 1:5,000 dilution (Pharmacia). The plates were developed using a commercial color kit (bioMérieux) containing OPD and $H_2O_2$. After 10 min of incubation, the plates were read at 492 nm with an ELISA plate reader. For each phage clone dilution, the results were expressed as the difference between the value obtained with the tested anti-HCV mAb and the value obtained with the irrelevant mAb. The results were then confirmed by testing optimal dilutions of the immunoreactive clones in triplicate.

For sequence analysis, the amino acid sequences of peptides were compared to the HCV E1 and E2 protein sequences by use of the Mac Vector, Ver. 4.5 software (Kodak). Basically, the regions of highest similarity were detected with the LFASTA program, which tentatively searches for best local identities (Pearson and Lipman, 1988).

After the three rounds of selection, 4% of the phage input were found in the eluate indicating amplification of specifically bound phages. Thus, 88 clones were randomly isolated, their DNA were sequenced and the amino acid sequences of inserts were deduced. Forty eight different sequences were obtained and some of them were found in several examples. However, when tested in an ELISA test for their immunoreactivity with D32.10, none of them gave a positive signal indicating that the binding affinity was too low to be detectable. The 48 clone sequences were compared to the sequences of HCV E1 and E2. Five and three sequences presented similarities with residues of E1 located in the 292-305 region and in the 347-356 region respectively (similarities are indicated in bold in Table 1), whereas 7, 4 and 2 sequences shared some similarities with residues of E2 located in the regions 481-501, 610-631 and 685-698 respectively (similarities are indicated in bold in Table 2).

TABLE 1

| E1 (289-307) | QLFTFSPRRHWTTTQGCNCS | (SEQ ID NO: 5) |
|---|---|---|
| Clone 1 | SPLRHYELPLIQ | (SEQ ID NO: 6) |
| Clone 2 | WPHNHSTHSRTH | (SEQ ID NO: 7) |
| Clone 3 | FPKYHPRFHKHA | (SEQ ID NO: 8) |
| Clone 4 | SQRSRHWHDVPK | (SEQ ID NO: 9) |
| Clone 5 | TSQPRWHQKPAT | (SEQ ID NO: 10) |

| E1 (343-363) | AILDMIAGAHWGVLAGIAYFS | (SEQ ID NO: 11) |
|---|---|---|
| Clone 6 | WKMPRATDWNLR | (SEQ ID NO: 12) |
| Clone 7 | HWGNHSKSHPQR | (SEQ ID NO: 13) |
| Clone 8 | WHRTPSTLWGVI | (SEQ ID NO: 14) |

TABLE 2

| E2 (481-501) | DQRPYCWHYPPKPCGIVPAKS | (SEQ ID NO: 15) |
|---|---|---|
| Clone 9 | WHKLPGHPRTV | (SEQ ID NO: 16) |
| Clone 4 | SQRSRHWHDVPK | (SEQ ID NO: 9) |
| Clone 10 | TFAWHKPRVNLG | (SEQ ID NO: 17) |
| Clone 11 | TSQPRWHQKPAT | (SEQ ID NO: 10) |
| Clone 12 | HSSWYIQHFPPL | (SEQ ID NO: 18) |
| Clone 13 | FPAHPLPRLPSL | (SEQ ID NO: 19) |
| Clone 8 | WHRTPSTLWGVI | (SEQ ID NO: 14) |

TABLE 2-continued

| E2 (610-631) | DYPYRLWHYPCTINYTIFKIRM | (SEQ ID NO: 20) |
|---|---|---|
| Clone 1 | SPLRHYELPLIQ | (SEQ ID NO: 6) |
| Clone 14 | WHWNKPIIRPPLR | (SEQ ID NO: 21) |
| Clone 15 | QPYKLQAAATLY | (SEQ ID NO: 22) |
| Clone 6 | WKMPRATDWNLR | (SEQ ID NO: 12) |

| E2 (685-698) | LSTGLIHLHQNIVD | (SEQ ID NO: 23) |
|---|---|---|
| Clone 16 | HLYHKNRNHHIAY | (SEQ ID NO: 24) |
| Clone 17 | WSPGQQRLHNST | (SEQ ID NO: 25) | b. Peptide Synthesis

In order to evaluate the significance of these different localizations on both E1 and E2 sequences, the regions 291-315 and 347-356 of E1 as well as the regions 473-498, 607-627 and 686-697 of E2 were reproduced as overlapping synthetic pentadecapeptides offset by one and tested for their immunoreactivity with D32.10.

The simultaneous synthesis of different peptide sequences was performed on a nitrocellulose membrane using 9-fluorenylmethoxycarbonyl aminoacid chemistry (Frank, 1988)

Each peptide was generated in nanomolar quantities suitable for immunological detection. Antibody reactivity to membrane bound peptides was analyzed by an indirect colorimetric immunoassay as described previously (Jolivet-Reynaud, 1998). Spots corresponding to peptides with antibody reactivity produced a positive blue signal. Intensity of spots was estimated by visualization and expressed as relative intensity on a scale ranging from 0 to 5.

A strong positive signal was obtained with peptides corresponding to the 292-305 E1 region whereas the 347-356 E1 region was not recognized by D32.10. Peptides corresponding to the E2 regions 482-499 and 612-626 respectively were also immunoreactive with D32.10 and no signal was detected with the E2 region 686-697. The regions 292-306 of E1 as well as the regions 480-494, and 608-622 of E2 as pentadecapeptides interacted with D32.10 in ELISA.

By using overlapping octapeptides, the $^{297}$RHWT-TQGCNC$^{306}$ (SEQ ID NO: 1) region of the HCV E1 protein and both $^{613}$YRLWHYPCT$^{621}$ (SEQ ID NO: 3) and $^{480}$PDQRPYCWHYPPKPC$^{494}$ (SEQ ID NO: 2) regions of the HCV E2 protein were reactive with D32.10. The two regions identified in E2 contain the same motif WHYP (SEQ ID NO: 28) suggested by Yagnik et al. (2000) to be involved in the heterodimerization of E1E2. Indeed it is difficult to discriminate these regions, but as two non overlapping zones: $^{479}$GPDQRPYC$^{486}$ (SEQ ID NO: 26) and $^{487}$WHYPP-KPC$^{494}$ (SEQ ID NO: 27) separately bound to D32.10, this suggests that D32.10 specifically recognizes each octapeptide, and so the complete sequence (480-494).

EXAMPLE 2

Characterization and Purification of Serum Derived HCV Viral Particles

To separate the different HCV populations, the final HCV-enriched pellet was subjected to isopycnic centrifugation (210,000 g for 48 h at 4° C.) in a sucrose density gradient (10 to 60%, w/w). Fractions (0.6 ml) were collected, and the density of each was determined by refractometry. HCV-RNA content was analyzed by quantitative RT-PCR (Amplicor Monitor, Roche), HCV core protein content was measured with the Ortho-Clinical Diagnostics test and the HCV viral particles antigenic reactivity towards mAb D32.10 was measured by indirect EIA.

Indirect EIA was carried out as indicated above except that the wells were coated with the different fractions diluted from $10^{-1}$ to $10^{-4}$.

Figure 4:
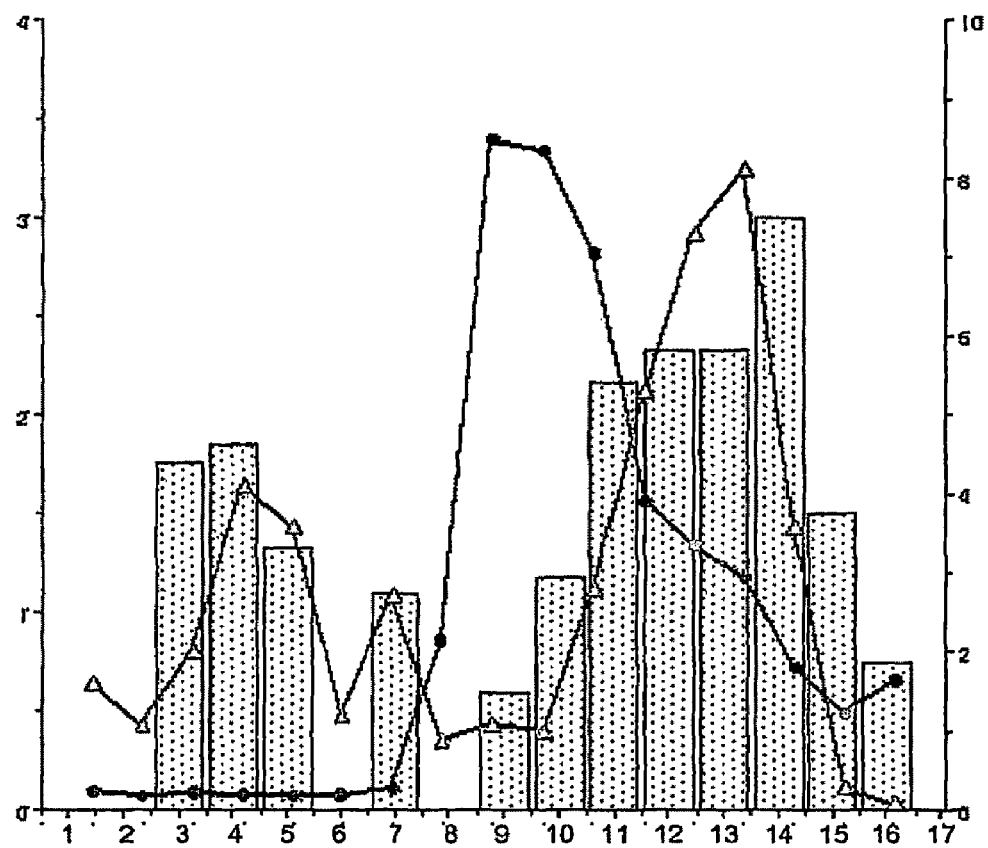
FIG. 4

Three different populations were identified (FIG. 4). One population (fractions 3 to 5) banded at a sucrose density of 1.06-1.08 g/ml and was substantially devoid of viral envelope as evidenced by the negative results obtained by indirect EIA with D32.10, but contained HCV RNA (about $2.10^5$ UI/ml) and HCV core protein (from about 2 to 4 pg/ml). These seem to be non-enveloped viral particles. Another population (fractions 8 to 10 of figure) banded at a sucrose density of 1.14-1.15 g/ml and was substantially devoid of HCV RNA (less than about $10^4$ to $10^5$ UI/ml) and of HCV core protein (about 1 pg/ml) but contained high levels of particles responding to D32.10 (from about 1 to 3.8 $OD_{450\ nm}$ units). These HCV subviral particles seem to contain only the HCV viral envelope. The third population (fractions 11 to 14) banded at a sucrose density of 1.20-1.21 g/ml and contained particles with high levels of HCV RNA (more than about $5.10^5$ to $10^6$ UI/ml) and of HCV core protein (from about 2.5 to 8 pg/ml) and responding to D32.10 (from about 0.5 to 1.5 $OD_{450\ nm}$ units). Hence, this population contains substantially only purified HCV enveloped complete viral particles.

Figure 5A:
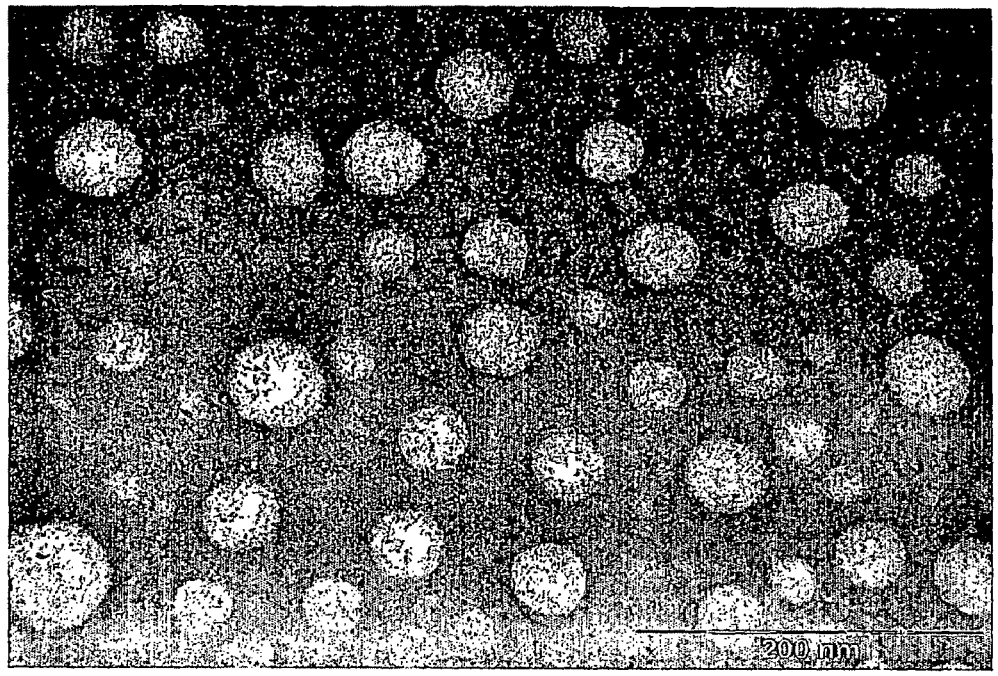
FIG. 5A, FIG. 5B and FIG. 5C
Figure 5B:
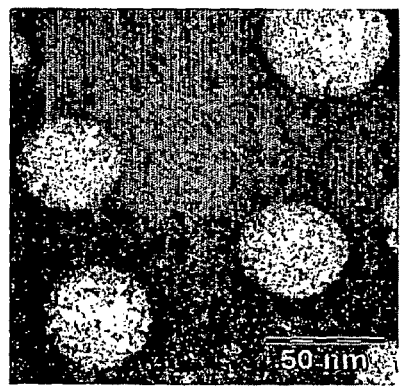
Figure 5C:
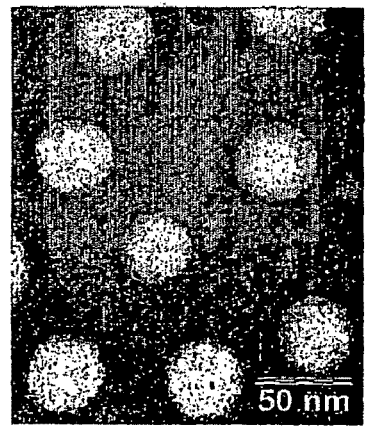

The viral particles contained in the HCV-enriched pellet (FIG. 5A), and in the second (FIG. 5C) and third populations (FIG. 5B) were immunoprecipitated by D32.10 and observed by electron microscopy. Several preparations of HCV viral particles have been analysed by this procedure The HCV enveloped subviral particles appear as spherical particles with an average diameter of about 30 nm (33.08 nm) (FIG. 5C), whereas the HCV enveloped complete viral particles appear equally spherical but with an average diameter of about 50 nm (48.72 nm) (FIG. 5B).

EXAMPLE 2bis

Characterization and Purification of Serum Derived HCV Viral Particles

Another analysis of the population of HCV viral particles present in the plasma of infected patients was also carried out by the inventors.
Purification of Serum-Derived HCV Particles The HCV enriched pellet obtained in Example 1 (HCV-L) was used for physico-chemical, immunological and morphological studies, as well as a pellet derived from the plasmapheresis of another patient (HCV-Fan, genotype 1a/2a), which showed chronic hepatitis C(CH—C) with type II cryoglobulinemia associated with severe cutaneous vascularitis, requiring regular plasma exchanges. As for the HCV-L patient, the latter HCV-Fan patient showed abnormal elevated serum aminotransferase (ALT/AST) levels, was positive for anti-HCV antibodies, and negative for all HBV and HIV markers.

Seven preparations were thus characterized. They were positive for HCV RNA from $10^6$ UI/ml to $2-3 \times 10^7$ UI/ml (HCV-Fan, HCV-L) in the quantitative Amplicor HCV RNA Monitor test (Roche), corresponding to $2.5 \times 10^6$ copies/ml to $5-7.5 \times 10^7$ copies/ml.

To separate the different HCV populations, the final HCV-enriched pellet was subjected to isopycnic centrifugation (200,000 g for 48 h at 4° C.) in a sucrose density gradient (10 to 60% or 30 to 45%, w/w). Fractions (0.6 ml) were collected, and the density of each was determined by refractometry. HCV-RNA content was monitored by quantitative RT-PCR (Amplicor Monitor, Roche). HCV envelope (env) reactivity was detected using MAb D32.10 by indirect EIA, as described above, after coating of each fraction at different dilutions (1/10 to 1/10000) on solid phase. HCV core antigen was assayed by using quantitative Ortho assay and western blotting using a mixture of anti-core monoclonal antibodies (7G12A8, 2G9A7 and 19D9D6) (Jolivet-Reynaud et al., 1998; Menez et al., 2003).

Briefly, the measurement of total HCV core antigen in the HCV-enriched pellets and in each fraction collected from sucrose gradient was performed by using Ortho$^R$ trak-C™ assay (Ortho-Clinical Diagnostics, Inc). Ortho$^R$ trak-C™ assay is a quantitative immuno-capture assay that uses several monoclonal antibodies with specificity to different regions of the HCV core antigen. The procedure uses a pretreatment step to make sample preparation free, immune-complexed, and virion associated antigen available to assay (Aoyagi et al., 1999). HCV RNA was assessed by a quantitative RT-PCR developed by Roche Molecular System (Meylan, France), Amplicor™ HCV Monitor™. The amplification step involves a single tube, single enzyme (rTth DNA polymerase), single primer pair combined reverse transcription and DNA polymerisation (Colucci and Gutekunst, 1997). The detection was performed by a colorimetric microwell plate assay. Control of PCR carryover contamination included AmpErase™ which has been incorporated into the assay to inactive contaminating amplified DNA (Longo et al., 1990).

The HCV-enriched pellets were first subjected to an isopycnic centrifugation in sucrose density gradient (10% to 60%). The presence of enveloped viral particles exhibiting E1E2-D32.10 reactivity was investigated by the indirect EIA method described above (FIGS. 14A and 14C) and western blotting (FIGS. 14B and 14D) using the anti-E1E2 MAb D32.10, the specificity of which was previously well-defined in Example 1. As shown in FIGS. 14A and 14C, E1E2-D32.10 reactivity in EIA (fraction diluted at 1/10000) was recovered from the fraction 9 (density of 1.12 g/ml) to the fraction 16 (density of 1.23 g/ml), with a peak between 1.12 and 1.17 g/ml, and a "shoulder" from 1.18 to 1.23 g/ml. No or very low D32.10 reactivity (fraction diluted at 1/10) was detected in fractions corresponding to the low-density complexes (1.006 to 1.10 g/ml). Similar results were obtained with the isolate HCV-L (FIG. 14A) of genotype 1b and with the isolate HCV-Fan (FIG. 14C) of genotype 1a/2a. Some fractions (6, 8, 10, 12, 14) of the isolate HCV-L (FIG. 14B) and all the fractions (4 to 18) of the isolate HCV-Fan were subjected to SDS-PAGE and western blotting with MAb D32.10. E1E2-D32.10 reactivity clearly appeared from fractions 8 (density # 1.10 g/ml) to the bottom of gradient. Noteworthy, the strongest E1E2 reactivity was observed in fractions 11, 12 and 13 (FIG. 14D) corresponding to the densities of 1.17 to 1.20 g/ml. Higher molecular weight (HMW) bands could be detected in these fractions, probably corresponding to oligomeric forms of E1 and E2 envelope glycoproteins present on the surface of viral particles banding at such densities. Another strong reactivity against both E2 and E1 was observed in fraction 9 (density of 1.13 g/ml) corresponding to the peak in EIA (FIG. 14C). All serum-derived HCV preparations gave the same equilibrium banding profiles of E1E2-D32.10 reactivity in sucrose density gradients (10 to 60%).

To further characterize the enveloped HCV populations, the HCV-Fan pellet was subjected to isopycnic centrifugation in a 30 to 45% sucrose gradient of type 1 (2 ml of 30%, 3 ml of 35%, 3 ml of 40%, 2 ml of 45%). Under these experimental conditions, two peaks of E1E2-D32.10 reactivity could be clearly individualized, as shown in FIG. 15A. Indirect EIA revealed a first narrow peak (Peak 1) at a density of about 1.15 g/ml, and a second wide large peak (Peak 2) at a density of about 1.18 g/ml to 1.22 g/ml. Particles from sucrose gradient (30-45%) peaks 1 (fraction 8) and 2 (fractions 12 and 13) were subjected individually to a second equilibrium centrifugation. Peak 1 was centrifuged in a 30 to 45% sucrose gradient of type 2 (3 ml of 30%, 3 ml of 35%, 2 ml of 40%, 2 ml of 45%) (FIG. 15B). Only one narrow E1E2 antigenic peak (Peak 1) migrated to a density of 1.13 to 1.14 g/ml (about 32% sucrose, fractions 5 and 6). Peak 2 was centrifuged in a 30 to 45% sucrose gradient of type 3 (2 ml of 30%, 2 ml of 35%, 3 ml of 40%, 3 ml of 45%) (FIG. 15C). A major peak (Peak 2) sedimented much faster, showing maximum E1E2 antigenicity at a density of about 1.18 g/ml (corresponding to 40% sucrose). The latter E1E2 antigenic peak (Peak 2) appeared asymmetric, moved forward the lower densities, and was slightly overlapped with E1E2 population banding at a sucrose density of 1.14 g/ml (Peak 1), suggesting a greater heterogeneity than the former E1E2 antigenic peak (Peak 1) (FIGS. 15B, 15C).

Figure 9A:
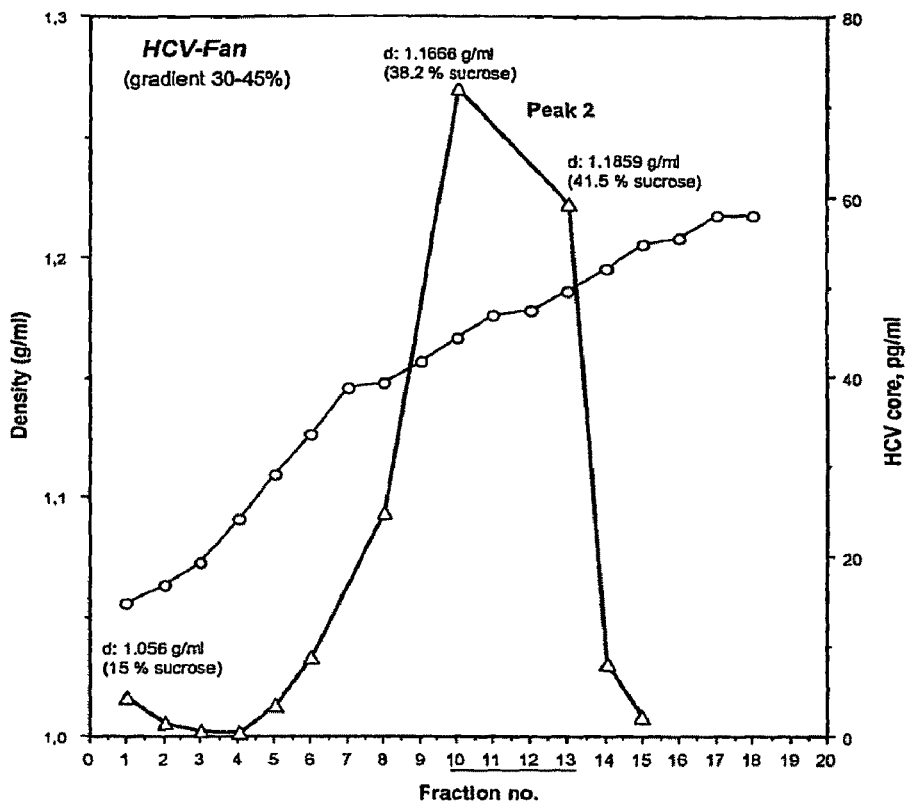
FIG. 9A and FIG. 9B

To elucidate the differences in buoyant density between the two populations of E1E2 enveloped viral particles (Peak 1 and Peak 2), the fractions from 30 to 45% sucrose gradient of type 1 described above were tested for HCV core antigen by the Ortho HCV core assay (FIG. 9A) and by Western blotting (FIG. 15B).

Briefly, the polypeptide specificity was determined by immunoblotting using HCV samples as antigenic probes (1-5 µg/ml). Sodium dodecyl sulfate (SDS)-polyacrylamide gel electrophoresis (PAGE) on 12.5% gels was performed under reducing conditions (2% SDS+5% 2-ME). After protein transfer onto PVDF membranes, anti-E1E2 MAb D32.10 (2 to 5 µg/ml) or anti-core MAbs 7G12A8, 2G9A7 and 19D9D6 (5 µg/ml each) were used as primary antibodies, diluted in 50% NHS, and IgGs bound were then detected by incubation with HRPO-conjugated (Fab')2 fragment of anti-mouse immunoglobulins (diluted 1/10,000; purchased from Immunotech), as second antibody. The blots were developed with an enhanced chemiluminescence (ECL Plus) system from Amersham.

Figure 9B:
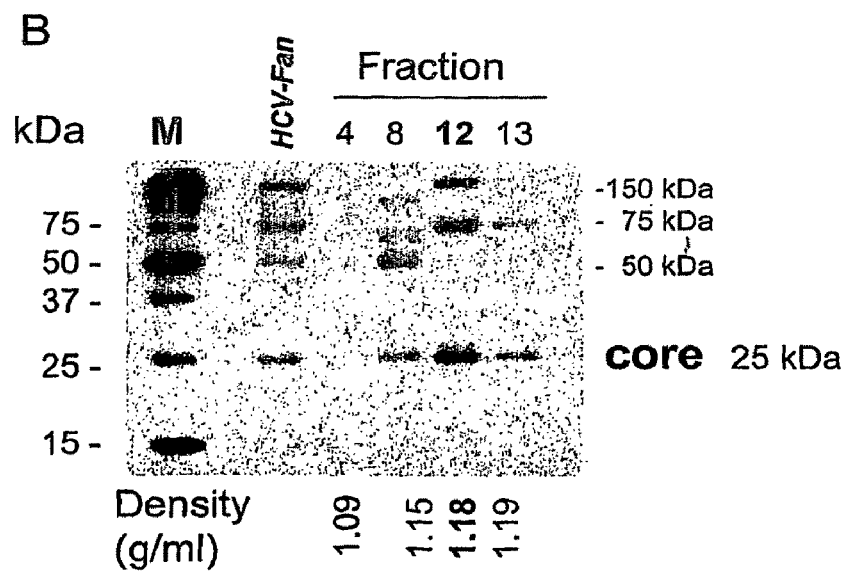
Figure 10:
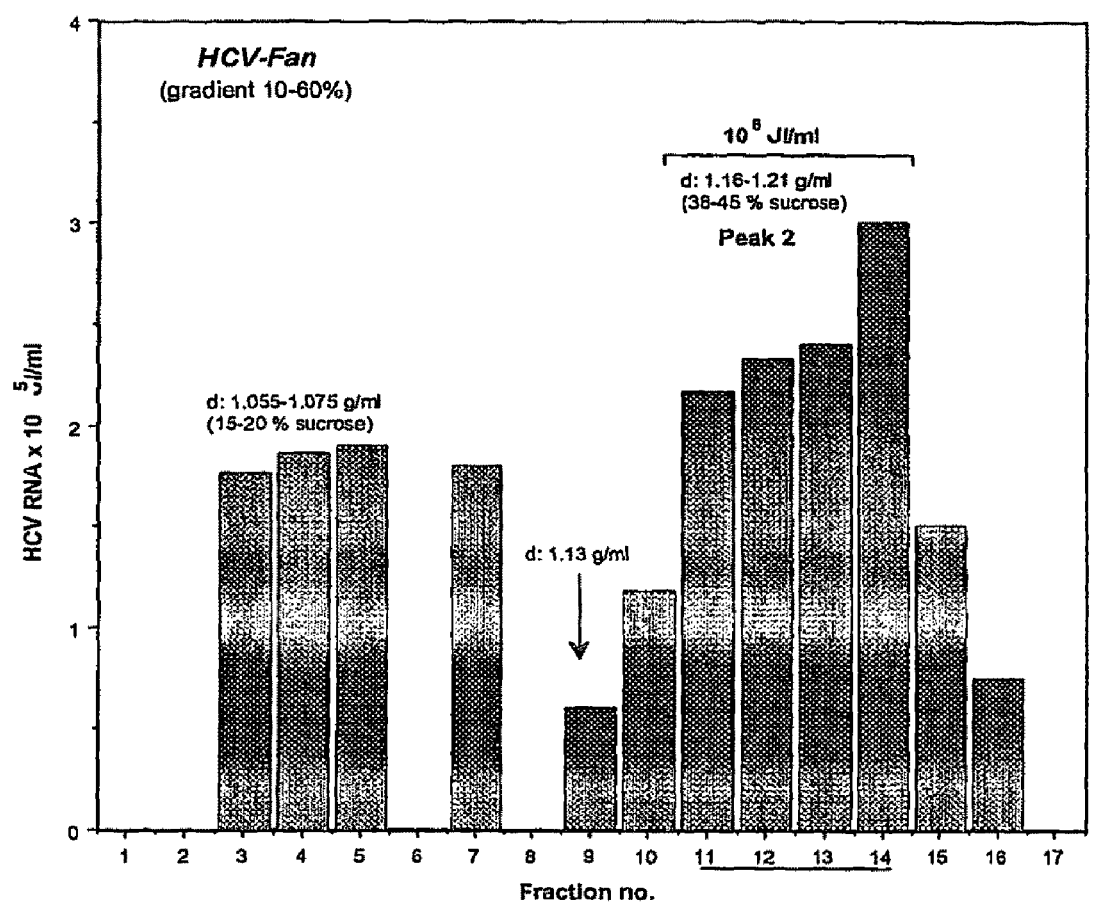
FIG. 10

Both experimental approaches showed that maximum HCV core antigen reactivity was recovered in the second E1E2 antigenic peak (Peak 2) at a density of approximately 1.17 to 1.19 g/ml (40% sucrose). By analysis in Western blotting (FIG. 9B), the HCV core protein of 25 kDa was identified in the initial material (HCV-Fan pellet) and fractions 8 to 13. Bands at 50, 75 and 150 kDa were also detected, which could correspond to oligomers of HCV core gene encoded-product. HCV RNA was analyzed by the quantitative RT-PCR Monitor test (Roche) in all the fractions from initial 10 to 60% sucrose gradient (FIG. 10). Two peaks of viral RNA occurred at a density of 1.055 to 1.075 g/ml, and at a density of 1.16 to 1.21 g/ml. Total titer of the latter peak was of $10^6$ IU/ml, and corresponded to the second E1E2 antigenic peak (Peak 2). In contrast, fraction 9 (density of 1.13 g/ml), which corresponded to Peak 1, contained the lowest titer of HCV RNA. Thus, peak 2 (approximately 1.17 to 1.20 g/ml) contained E1E2 complexes, HCV core protein, high titer of HCV RNA and is likely to represent complete virions. Peak 1 (1.13 to 1.15 g/ml) contained mainly E1E2 complexes and is likely to represent subviral particles (SVPs). The low density complexes (1.006 to 1.10 g/ml) contained only core and HCV RNA, corresponding to naked nucleocapsids.

Thus, using the D32.10 monoclonal antibody of the invention, the most prevalent types of enveloped viral particles found in the serum of chronic hepatitis C patients have been analyzed. By sedimentation in sucrose gradients of concentrated viral material, analysis of the protein composition (core and envelope proteins) by immunoassays and immunoblotting, coupled with monitoring of HCV RNA by quantitative RT-PCR, two populations of E1E2 enveloped particles which sedimented at two distinct densities of 1.13-1.15 g/ml and 1.17-1.21 g/ml, were identified respectively. The first population corresponded to subviral particles (SVPs) containing the E1 and E2 envelope proteins, but lacking nucleocapsids. The second population could correspond to HCV virions, since these particles contained the E1 and E2 envelope proteins, the core proteins and high titer of HCV RNA.

Morphological Characterization of Serum-Derived HCV Particles

Electron microscopy of HCV-Fan pellet after immunoprecipitation by E1E2(D32.10)-specific monoclonal antibody (immuno-electron microscopy or IEM), was performed according to the following procedure.

Briefly, serum-derived HCV preparations (2, 20 or 200 µg) or fractions from the gradients (0.1 ml) were mixed with 0.1 ml of MAb D32.10 (5 µg) or irrelevant monoclonal antibody (F35.25, HBV anti-preS1) (Petit et al., 1989) of the same isotype (IgG1). Incubation was performed at 37° C. for 1 h, then at 4° C. for 16 h. The mixture was then diluted in 10 ml of TNE buffer and centrifuged at 48,000 g for 1 h. The pellet was resuspended in 0.1 ml of TNE buffer. D32.10-immunoprecipitated HCV particles were absorbed for 5 min onto glow-discharged Formvar/carbon-coated cupron grids and stained for 4 min with 1% uranyl acetate (pH 4.5). The preparations were then visualized using a JEOL 100 CX electron microscope (Imaging facility, Laennec Faculty, Lyon, France). For indirect immuno-gold labeling, the grids were incubated with a 1:50 dilution of goat anti-mouse IgG-colloidal gold particles (10-nm diameter; BioCell Research Laboratories), as second antibody.

Figure 13:
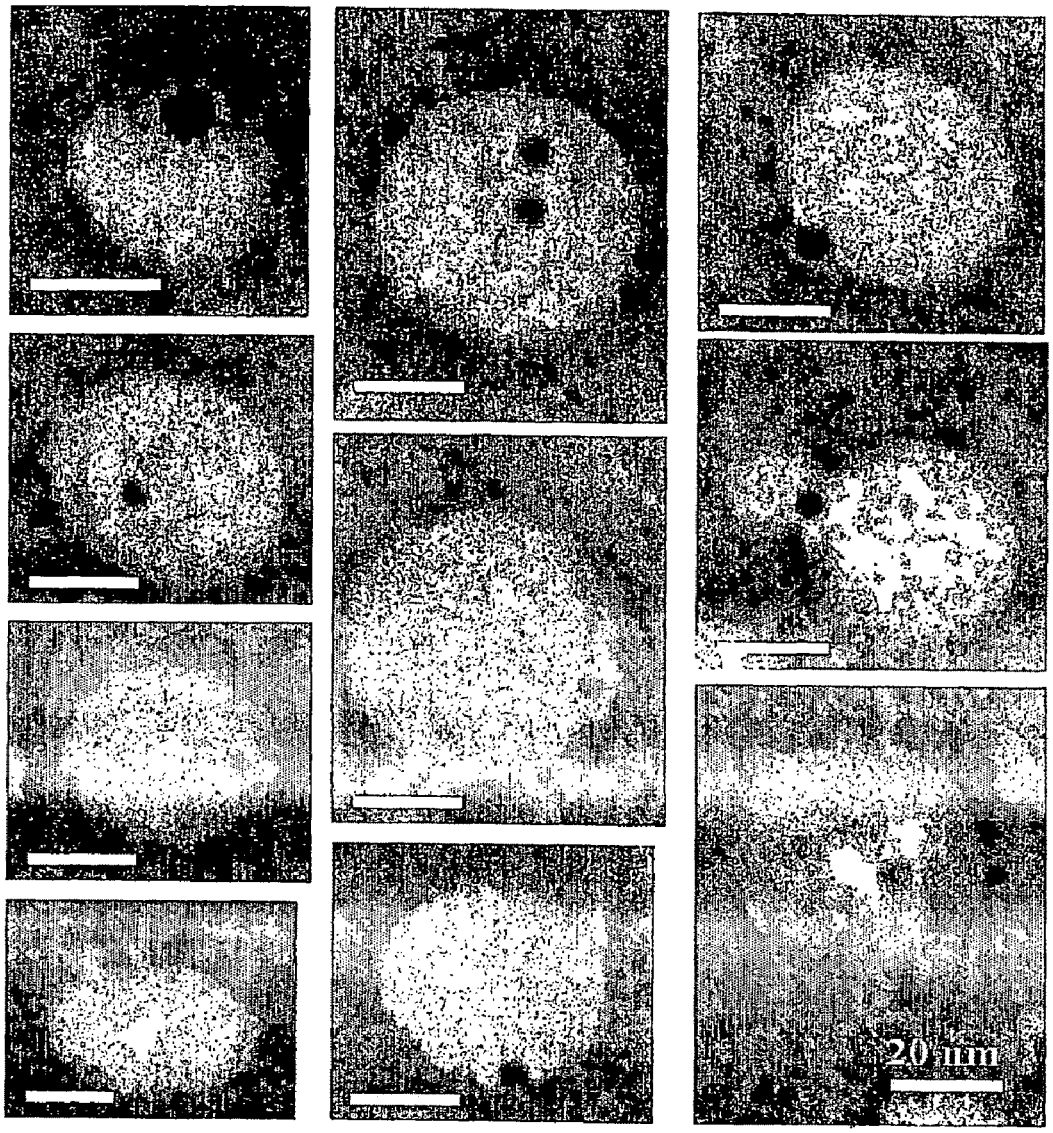

Control experiments showed that the size heterogeneity of preparations varied with the antigen:antibody ratio (results not shown). In order to preserve morphological integrity, isolation procedure of HCV particles involved only precipitation and sucrose gradient centrifugation. Under such experimental conditions, a relatively well-defined particle size distribution pattern was obtained, as shown in FIG. 11A. The asymmetric peak centered at about 35 nm. Particles of this size (30 to 40 nm) were predominant (56%). Essentially the majority of particles (80%) had a diameter greater than 30 nm, with a mean value of 38.28 nm (125 out of 156 particles), 20% of them between 40 to 50 nm (mean value=43.61 nm) and 4% between 50 and 60 nm (mean value=55.69 nm). Only 20% of all particles had a diameter smaller than 30 nm (mean value=26.35 nm). Electron micrographs (FIG. 11B) showed that HCV particles are characterized by a relatively regular smooth surface. FIG. 11B, panels a and b, illustrate the heterogeneity in size of HCV enveloped particles. FIG. 11B, panel c shows particles with a diameter of 50 nm, and panel d those with a diameter of 35 nm. A quite homogenous higher density appeared on the surface of particles of 35 nm (FIG. 11B, panel d), whereas a lighter area of lower density could be clearly observed in the center of particles with a diameter of 50 nm (FIG. 11B, panel c). No particles were visualized by IEM when using an irrelevant primary monoclonal antibody (FIG. 11B, panel e). Particles from sucrose gradient peaks 1 and 2 were immunoprecipitated, stained, and also analyzed by IEM (FIG. 12A-12B). As shown in FIG. 12A, the predominant species (85.4%) in peak 1 was a spherical particle with a diameter of about 20 nm (35 out of 41 particles, mean value=20.6 nm). Only 14.6% of particles had a diameter greater than 30 nm, probably corresponding to an overlap with peak 2. Peak 2 appeared somewhat more heterogeneous in size than the peak 1 material (FIG. 12B). However, the most prevalent forms (77.5%) in this population had a mean diameter of about 41 nm (69 out of 89 particles, mean value=41.15 nm), which could correspond to the diameter of the whole HCV virion. A few of the smaller 30-nm-diameter particles (13.5%) were visible in this preparation, and probably result from an overlap with peak 1. The heterogeneous major faster-sedimenting peak (Peak 2) consisted primarily of 35 and 50-nm-diameter large particles, whereas the homogeneous minor slower-sedimenting peak (Peak 1) consisted of approximately 20-nm-diameter small particles. Taken together, the morphological studies indicate that two size classes of E1E2 enveloped HCV particles co-exist in the serum of infected patients. By indirect immuno-gold labeling (FIG. 13), all spherical enveloped particles, previously identified by IEM, specifically fixed 10-nm-gold-labeled secondary antibody.

Thus, by immuno-electron microscopy with MAb D32.10, a relatively well-defined particle size distribution of the total enveloped population (HCV-enriched pellet) and of each E1E2 population separately, was determined. The enveloped HCV particles are heterogenous in size, but two distinct size classes of particles could be readily identified. A predominant species consisted of large particles with a diameter which varied from 35 nm to 50 nm, likely depending on the lattice structure of the envelope, corresponding to complete capsid-containing enveloped particles. Another more homogenous species consisted of small particles with a diameter of about 20 nm, corresponding to capsidless SVPs. All these particles which bound to MAb D32.10 were further identified and visualized by electron microscopy using an indirect labelling with anti-mouse IgG-gold particles.

Formation of noninfectious SVPs, in addition to infectious virions, is a common characteristic of flavivirus infections (Russel et al., 1980). It has been suggested that these represent capsidless empty viral envelopes (Mason et al., 1991). It also occurs in cells infected with hepatitis B virus (HBV), and secreted SVPs are produced by expression of envelope proteins alone (Laub et al., 1983). These particles are smaller than virions. This demontrates that these proteins are intrinsically capable of self-forming specific particulate structures in the presence or absence of a core. These particles are assembled and undergo the same maturation process as the whole virions, including glycosylation and carbohydrate processing. Immunization with such recombinant envelope SVPs shows them to be excellent protective immunogens in animal models (Konishi et al., 1992; Heinz et al, 1995) as well as in humans (Leroux-Roels et al., 1994).

The reactivity of complete virions and SVPs with MAb D32.10 shows that E1(297-306)-E2(480-494)(613-621) conformational epitope is presented in essentially the same way on the surfaces of HCV virions and SVPs. However, such epitope detected on virions and SVPs derived from serum is lacking on particles obtained by genetic recombination and produced in heterologous systems: baculovirus/insect cells (Baumert et al., 1999) or retrovirus/293T cells (Bartosch et al., 2003), suggesting that this composite site is either absent and/or present on separate inaccessible regions on the surfaces of these recombinant HCV particles. The former HCV-like particles (HCV-LPs) were retained in the ER, and only a small fraction of the latter HCV pseudo-particles (HCVpp) reached the cell surface. It is worth noting that MAb D32.10 is not reactive with either HSA or with γ- or µ-chains of immunoglobulins. It is able to specifically immunoprecipitate E1, E2, as well as E1E2 heterodimers, when these two proteins are expressed separately or together by vaccinia virus recombinants in HepG2 cells. It thus reacts mostly with disulfide-bond linked-aggregates and more faintly with E1E2 non covalently-linked mature complex. However, it does not recognize denatured recombinant E1 or E2 proteins expressed in such an heterologous system by blotting analysis. This is in favour of an arrangement of E1,E2 and E1E2 on the serum-derived virus surface which is different from the one found in recombinant HCV particles. The natural structure depends on assembly conditions. If the conditions that regulate formation of a unique structure are absent in heterologous systems, the dimer arrangement in the VLPs and HCVpp is not similar, contrasting with the similarity of SVPs and virion surfaces, when both are isolated from the serum of infected patients. One particularly noteworthy feature of the packing of the envelope proteins (E) of flaviviruses, including tick-born encephalitis virus (TBEV), in recombinant subviral particles (RSPs) and virions, is that they lie flat on the viral surface, in a head-to-tail orientation (Ferlengi et al., 2001). The lateral surface on domain III, which has an Ig-like fold and is implicated in receptor binding, is accessible, while the fusion peptide is an internal loop (Rey et al., 1995). So, flaviviruses enter cells by receptor-mediated endocytosis and low-pH-induced fusion in endosomes (Rice, 1996). An assembling particle is believed to acquire its envelope by budding through the membrane of the ER or an intermediate compartment of the early secretory pathway. The particles are then transported through the trans-Golgi network (TGN) to the plasma membrane, mature and so acquire complex sugars. All these steps are crucial for virus assembly and play a critical role in many phases of the replication cycle.

Unexpectedly, all HCV particles seemed to exhibit similar biophysical properties whatever their origin. The sucrose gradient sedimentation pattern of HCV-LPs assembled in insect cells, derived from strain HCV-J cDNA or from infectious clone H77c, was 1.14 to 1.20 g/ml in sucrose equilibrium gradients (WelLnitz et al., 2002). The majority of particles had a diameter of 40 to 60 nm. However, all epitopes presented on the E1 and E2 ectodomains of the outer surface of the HCV-LPs (WelLnitz et al., 2002) are distinct from the E1 and E2 specificity of MAb D32.10. So, even if the particles sediment at the same density in sucrose, they possess different immunoreactivities, which may be linked to an improper transport and/or folding, and obviously will result in different functional properties, in terms of cell binding and infectivity.

Contrary to serum enveloped HCV particles, HCV core particles isolated from the plasma of HCV-infected individuals seem to be similar to nucleocapsid-like particles produced in insect cells. HCV nucleocapsids banded at a density of 1.32 to 1.34 g/ml in the CsCl gradient and were very heterogenous in size, 38 to 62 nm in diameter (Maillard et al., 2001). All these particles were reactive with anti-core MAbs, but not with anti-E1 and anti-E2 MAbs produced by immunization with recombinant proteins (Deleersnyder et al., 1997; Dubuisson et al., 1994).

So, different types of HCV-related particles (HCV-LPs, serum HCV nucleocapsids, serum HCV virions) possess some similarities in size and/or in density, but exhibit different antigenic properties (improper or proper folding of E1E2 complexes, enveloped virions or nonenveloped nucleocapsids). Therefore, altogether this demontrates that it is crucial to have good immunological tools for analyzing the true antigenic properties of HCV particles, and so for identifying the natural HCV virions.

In the light of these data and those of others (Andre et al., 2002; Maillard et al., 2001), a better knowledge of complete spectrum of different forms of HCV-related particles circulating in the serum of chronic hepatitis C patients could be acquired. Low-density fractions in sucrose gradient (1.06 g/ml) contained capsid-like structures, associated with lipoproteins to form lipo-viro-particles (LVP), and with HCV RNA and immunoglobulins depending on individual variations (Andre et al., 2002). LVP appeared as large particles of more than 100 nm in-diameter, and bound hepatocyte cell line through the LDL receptor (Andre et al., 2002). Nonenveloped HCV nucleocapsids isolated from detergent treated sera had a buoyant density of 1.32 to 1.34 g/ml in CsCl, were heterogeneous in size (Maillard et al., 2001), and were recently shown to exhibit FγR-like activity (Maillard et al., 2004), which could explain the association of HCV RNA-containing particles with "non-immune" antibodies as HCV core-IgG complexes as high-density (1.28 to 1.35 g/ml) in sucrose gradient. The fractions of intermediate density, between 1.13 to 1.21 g/ml, were identified here as E1E2 enveloped HCV particles. The average density of the presumptive entire HCV virion (1.18 to 1.20 g/ml), consisting of a nucleocapsid, lipid membrane, and two E1 and E2 envelope glycoproteins, is similar to that of the flaviviruses (Bradley et al., 1991). The hypothesis of lateral envelope protein interactions, deduced from the fine specificity of MAb D32.10, is also similar to organization of the envelope of recombinant SVPs from TBEV and whole virus particles (Schalich et al., 1996). Finally, the presence in serum of HCV-infected patients of SVPs containing only the E1E2 envelope proteins, showing different sedimentation properties (1.13 to 1.15 g/ml) and different particle sizes (≈20 nm) but similar antigenic characteristics as whole virus particles, supports some similarities between HCV and the flaviviruses.

In conclusion, by using a new MAb D32.10, were identified for the first time:
  (i) HCV complete virions, containing both HCV RNA and core antigen, and expressing E1E2 envelope complexes on their surface, as "large particles", with a diameter of 35-50 nm and banding at 1.17-1.21 g/ml;
  (ii) an HCV population of envelope SVPs, as "small particles", devoid of capsid and HCV RNA with a diameter of 20-30 nm and banding at 1.13-1.15 g/ml.

Such enveloped particles may therefore represent a relevant model for investigating HCV envelope glycoprotein structure-function relationship, and an excellent candidate for vaccination approaches. In addition, it will be interesting to follow the spectrum of circulating HCV particles up in different groups of patients, and at different stages of the HCV-related disease.

EXAMPLE 3

Figure 6:
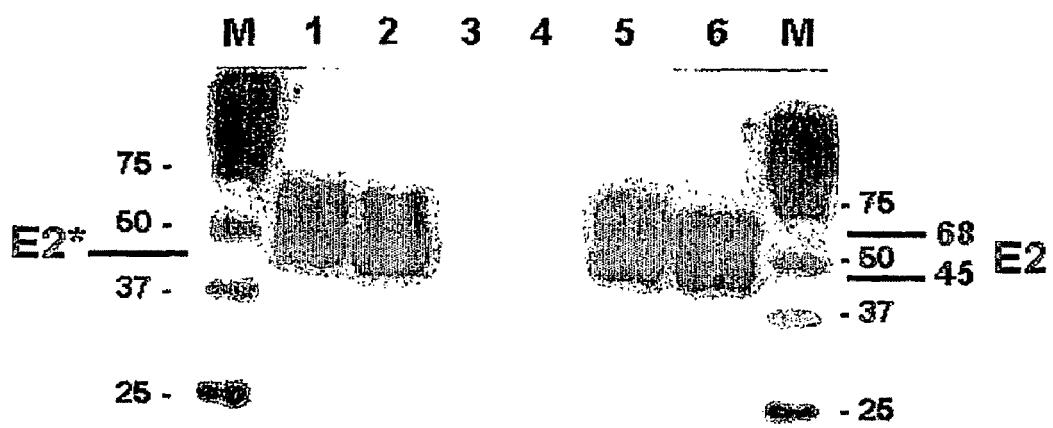
FIG. 6
Figure 7:
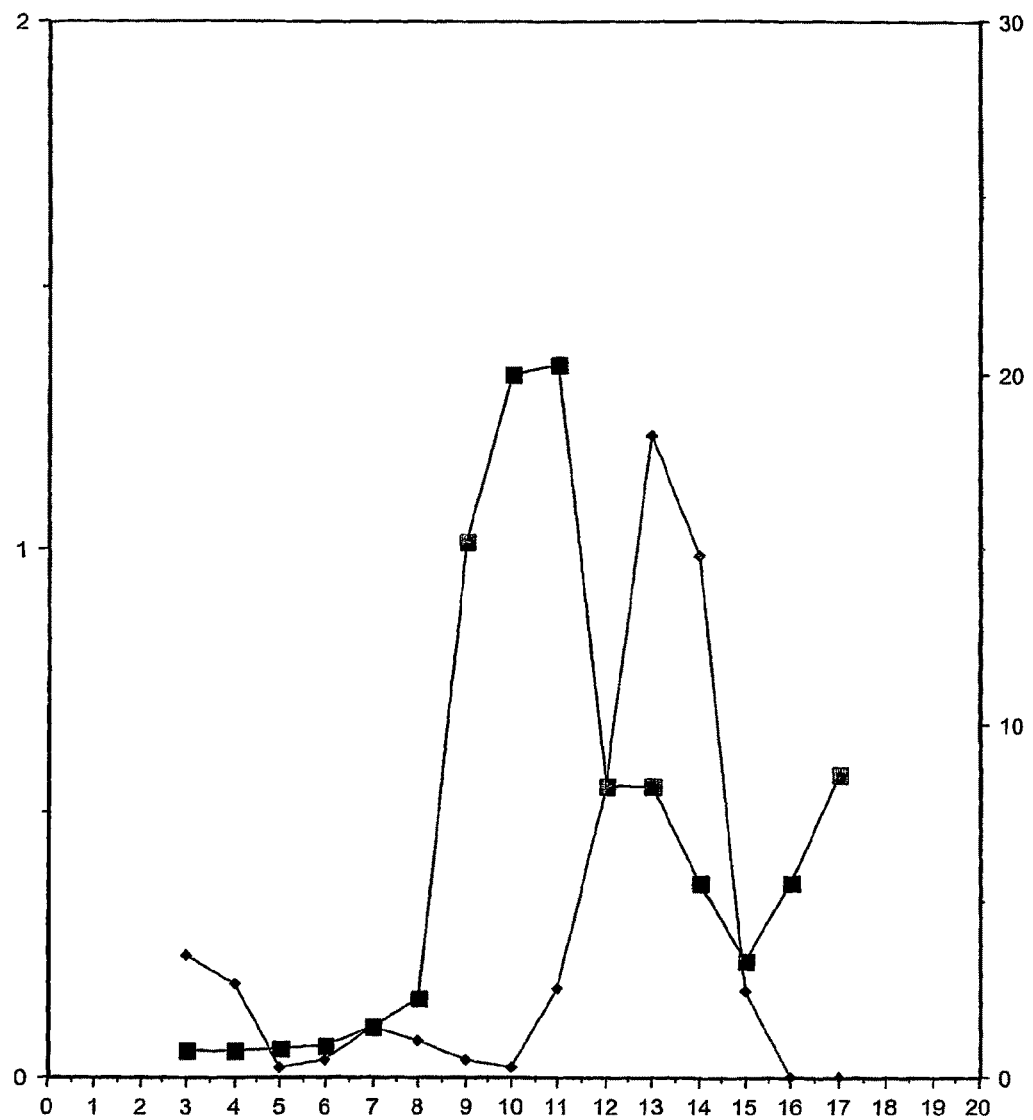
FIG. 7

Obtaining of a Monoclonal Antibody Directed Against Purified HCV Enveloped Complete Viral Particles The fraction of the above mentioned HCV-enriched pellet subjected to isopycnic centrifugation in a sucrose density gradient, containing the purified HCV enveloped complete viral particles, was used to prepare a monoclonal antibody. This fraction was used to immunize mice and isolate hybridomas as explained above. Thus, one monoclonal antibody, (D4.12.9) was obtained, which was shown to specifically recognize the natural HCV E2 protein in Western blotting experiments (FIG. 6) and the natural HCV viral particles evidenced in Example 2 (FIG. 7). Indeed, FIG. 7 shows that D4.12.9 recognizes both the HCV enveloped subviral particles (fractions 8 to 11) and the HCV enveloped complete viral particles (fractions 11 to 14), in a manner similar to D32.10.

EXAMPLE 4

Epitopic Characterization of Anti-HCV Antibodies Derived from Infected Patients

The immunoreactivity of the E1 and E2 derived peptidic sequences reactive with D32.10 (Example 1) towards sera of HCV-infected patients was assessed by using peptides encompassing them.

E1 (amino acids 290-317) and E2 (amino acids 471-500 and 605-629) sequences were produced as biotinylated synthetic peptides to be tested by ELISA with 11 sera from healthy individuals and 44 sera from HCV-infected patients (numbered A1 to A44).

The wells of microtitration plates were coated overnight at 4° C. with 100 µl of streptavidin at the concentration of 10 µg/ml in 0.1 M carbonate buffer (pH 9.6) and blocked for 1 h at 37° C. with PBS containing 10% goat serum. The plates were then washed three times with PBS containing 0.05% Tween -20 before adding 100 µl of a biotinylated peptide solution (10 µg/ml in PBS) for 2 h at 37° C. After a new wash with PBS-Tween, 100 µl of the tested serum diluted 1:50 in PBS-Tween containing 10% goat serum was added and incubated for 2 h at 37° C. The plates were washed again with PBS-Tween. The secondary antibody, peroxydase-conjugated goat anti-human IgG (Jackson ImmunoResearch Laboratories), was then added at a 1:5000 dilution in PBS-Tween-goat serum. The plates were incubated 1 h at 37° C. and then washed once more with PBS-Tween. The plates were developed using the Biomerieux color kit containing o-phenylenediamine and hydrogen peroxide. After 10 min of incubation, the plates were read at 492 nm with an ELISA plate reader. The reported values are the mean OD of triplicate.

Figure 8A:
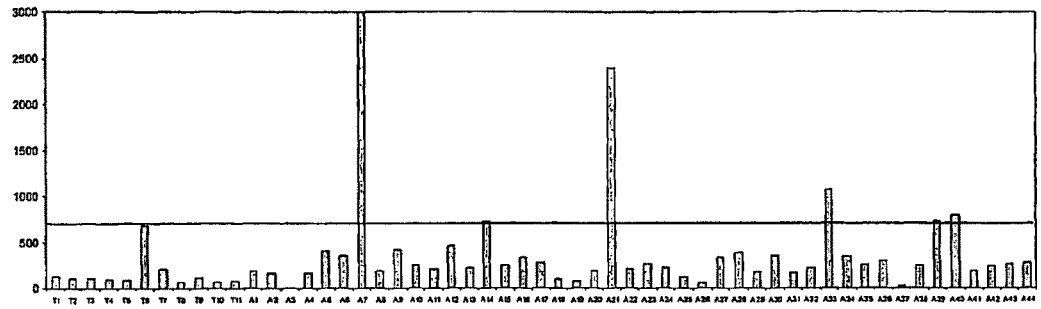
FIG. 8A, FIG. 8B and FIG. 8C
Figure 8B:
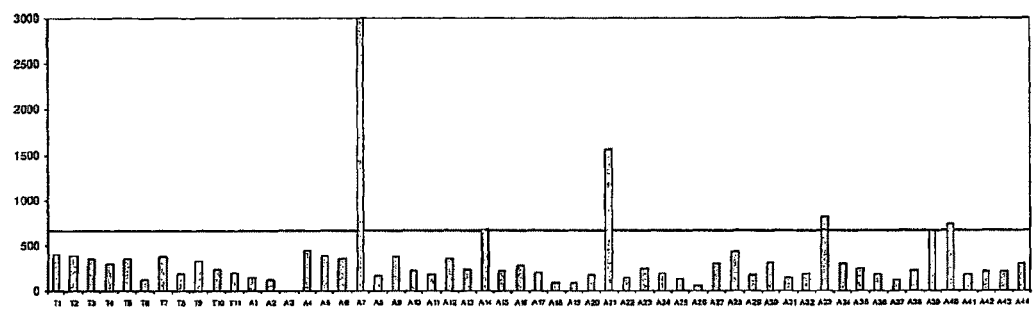
Figure 8C:
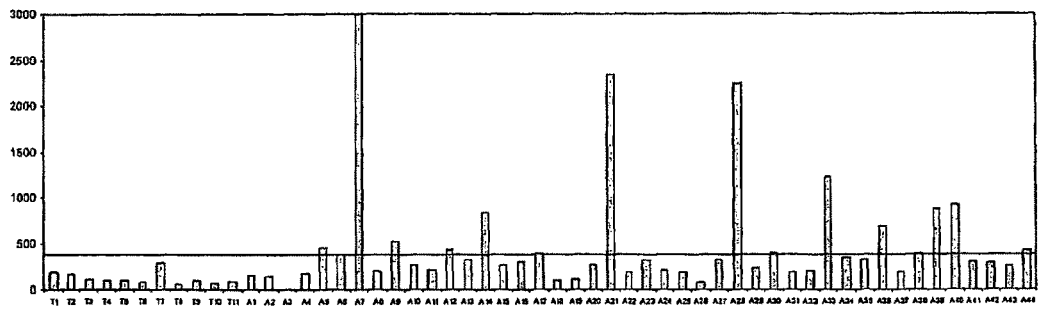

A cut off recognition was calculated for each peptide (mean of the values obtained with HCV negative sera+3 standard deviations). It allowed to evidence positive responses with 6 out of 44 HCV-positive sera against E1 (amino acids 290-317) (FIG. 8A), 6 out of 44 against E2 (amino acids 471-500) (FIG. 8B) and 16 out of 44 against E2 (amino acids 605-629) (FIG. 8C). Sera A7, A14, A21, A33, A39 and A40 gave a positive signal with the three peptides whereas E2 (605-629) was also recognized by 10 more sera.

The presence in the sera of HCV-infected patients of specific antibodies able to react simultaneously with the three regions of E1 and E2 recognized by D32.10 mAb strongly supports their juxtaposition at the surface of circulating enveloped HCV viral particles and their immunogenicity in mice as well as in humans.

REFERENCES

Andre, P., F. Komurian-Pradel, S. Deforges, M. Perret, J. L. Berland, M. Sodoyer, S. Pol, C. Brechot, G. Paranhos-Baccala, and V. Lotteau. 2002. Characterization of low- and very-low-density hepatitis C virus RNA-containing particles. *J Virol* 76:6919-28

Aoyagi K, Ohue C, Iida K, Kimura T, Tanaka E, Kiyosawa K, Yagi S. *J. Clin. Microbiol.* (1999) 37:1802-1808

Bartenschlager R, Lohman V. *J. Gen. Virol.* (2000) 81:1631-1648

Bartosch, B., J. Dubuisson, and F. L. Cosset. 2003. Infectious hepatitis C virus pseudo-particles containing functional E1-E2 envelope protein complexes. *J Exp Med* 197:633-42.

Baumert, T. F., J. Vergalla, J. Satoi, M. Thomson, M. Lechmann, D. Herion, H. B. Greenberg, S. Ito, and T. J. Liang. 1999. Hepatitis C virus-like particles synthesized in insect cells as a potential vaccine candidate. *Gastroenterology* 117:1397-407.

Bradley, D., K. McCaustland, K. Krawczynski, J. Spelbring, C. Humphrey, and E. H. Cook. 1991. Hepatitis C virus: buoyant density of the factor VIII-derived isolate in sucrose. *J Med Virol* 34:206-8.

Buttin B, Leguern C, Phalente L, Lin E C C, Medrano L, Cazenave P A. *Curr. Top. Microbiol. Immun.* (1978) 81:27-36

Choo Q L, Kuo G, Weiner A J, Overby L R, Bradley D W, Houghton M. *Science* (1989) 244:359-362

Choo Q L, Richman K H, Han J H, Berger K, Lee C, Dong C, Gallegos C, Coit D, Medina-Selby R, Barr P J, et al. *Proc. Natl. Acad. Sci. USA* (1991) 88:2451-2455

Clarke B. *J. Gen. Virol.* (1997) 78:2397-410

Colucci, G., and K. Gutekunst. 1997. Development of a quantitative PCR assay for monitoring HCV viraemia levels in patients with chronic hepatitis C. *J Viral Hepat* 4 Suppl 1:75-8.

Damen M, Sillekens P, Cuypers H T, Frantzen I, Melsert R. *J. Virol. Methods* (1999) 82:45-54

Deleersnyder V, Pillez A, Wychowski C, Blight K, Xu J, Hahn Y S, Rice C M, Dubuisson J. *Journal of Virology* (1997) 71:697-704

Dubuisson, J., H. H. Hsu, R. C. Cheung, H. B. Greenberg, D. G. Russell, and C. M. Rice. 1994. Formation and intracellular localization of hepatitis C virus envelope glycoprotein complexes expressed by recombinant vaccinia and Sindbis viruses. *J Virol* 68:6147-60.

Dubuisson J, Rice C. *Journal of Virology* (1996) 70:778-786

Dubuisson J. *Current Topics in Microbiology and Immunology* (2000) 242:135-148

Ferlenghi, I., M. Clarke, T. Ruttan, S. L. Allison, J. Schalich, F. X. Heinz, S. C. Harrison, F. A. Rey, and S. D. Fuller. 2001. Molecular organization of a recombinant subviral particle from tick-borne encephalitis virus. *Mol Cell* 7:593-602.

Frank R, Döring R. *Tetrahedron* (1988) 44:6031-6040

Heinz, F. X., S. L. Allison, K. Stiasny, J. Schalich, H. Holzmann, C. W. Mandl, and C. Kunz. 1995. Recombinant and virion-derived soluble and particulate immunogens for vaccination against tick-borne encephalitis. *Vaccine* 13:1636-42.

Hijikata, M., Y. K. Shimizu, H. Kato, A. Iwamoto, J. W. Shih, H. J. Alter, R. H. Purcell, and H. Yoshikura. 1993. Equilibrium centrifugation studies of hepatitis C virus: evidence for circulating immune complexes. *J Virol* 67:1953-8.

Jolivet-Reynaud C, Dalbon P, Viola F, Yvon S, Paranhos-Baccala G, Piga N, Bridon L, Trabaud M A, Battail N, Sibai G, Jolivet M. *J Med Virol* (1998) 56:300-309

Kanto, T., N. Hayashi, T. Takehara, H. Hagiwara, E. Mita, M. Naito, A. Kasahara, H. Fusamoto, and T. Kamada. 1995. Density analysis of hepatitis C virus particle population in the circulation of infected hosts: implications for virus neutralization or persistence. *J Hepatol* 22:440-8

Kohler G, Milstein C. *Nature* (1975) 256:495-497

Konishi, E., S. Pincus, E. Paoletti, R. E. Shope, T. Burrage, and P. W. Mason. 1992. Mice immunized with a subviral particle containing the Japanese encephalitis virus prM/M and E proteins are protected from lethal JEV infection. *Virology* 188:714-20.

Laub, O., L. B. Rall, M. Truett, Y. Shaul, D. N. Standring, P. Valenzuela, and W. J. Rutter. 1983. Synthesis of hepatitis B surface antigen in mammalian cells: expression of the entire gene and the coding region. *J Virol* 48:271-80.

Leroux-Roels, G., E. Van Hecke, W. Michielsen, P. Voet, P. Hauser, and J. Petre. 1994. Correlation between in vivo humoral and in vitro cellular immune responses following immunization with hepatitis B surface antigen (HBsAg) vaccines. *Vaccine* 12:812-8.

Longo, M. C., M. S. Beminger, and J. L. Hartley. 1990. Use of uracil DNA glycosylase to control carry-over contamination in polymerase chain reactions. *Gene* 93:125-8.

Lowry O, Rosebrough A, Farr A, Randall R. *J. Biol. Chem.* (1951) 193:265-275

Maillard, P., K. Krawczynski, J. Nitkiewicz, C. Bronnert, M. Sidorkiewicz, P. Gounon, J. Dubuisson, G. Faure, R. Crainic, and A. Budkowska. 2001. Nonenveloped nucleocapsids of hepatitis C virus in the serum of infected patients. *J Virol* 75:8240-50.

Maillard, P., J. P. Layergne, S. Siberil, G. Faure, F. Roohvand, S. Petres, J. L. Teillaud, and A. Budkowska. 2004. Fc{gamma} Receptor-like Activity of Hepatitis C Virus Core Protein. *J Biol Chem* 279:2430-2437.

Mason, P. W., S. Pincus, M. J. Fournier, T. L. Mason, R. E. Shope, and E. Paoletti. 1991. Japanese encephalitis virus-vaccinia recombinants produce particulate forms of the structural membrane proteins and induce high levels of protection against lethal JEV infection. *Virology* 180:294-305.

Menez, R., M. Bossus, B. H. Muller, G. Sibai, P. Dalbon, F. Ducancel, C. Jolivet-Reynaud, and E. A. Stura. 2003. Crystal structure of a hydrophobic immunodominant antigenic site on hepatitis C virus core protein complexed to monoclonal antibody 19D9D6. J Immunol 170:1917-24.

Op De Beeck A, Cocquerel L, Dubuisson J. *J. Gen. Virol.* (2001) 82:2589-95

Pearson W R, and Lipman D J. *Proc Natl Acad Sci USA* (1988) 85:2444-2448

Petit M A, Capel F, Riottot M M, Dauguet C, Pillot J. *J. Gen. Virol.* (1987) 68:2759-2767

Petit, M. A., S. Dubanchet, and F. Capel. 1989. A monoclonal antibody specific for the hepatocyte receptor binding site on hepatitis B virus. *Mol Immunol* 26:531-7.

Rey, F. A., F. X. Heinz, C. Mandl, C. Kunz, and S. C. Harrison. 1995. The envelope glycoprotein from tick-borne encephalitis virus at 2 A resolution. *Nature* 375:291-8.

Rice, C. 1996. Flaviviridae: the viruses and their replication, p. 931-959. In K. D. Fields B N, Howley P M, Chanock R M, Melnick J L, Monath T P, Roizman B, and Straus S E (ed.), Virology. Lippincott-Raven, Philadelphia, Pa.

Russell, P., Brandt W E and Dalrymple J M. 1980. Chemical and antigenic structure of flaviviruses, p. 503-529. In S. R W (ed.), The Togaviruses. Biology, Structure, Replication. Academic Press, New York.

Sambrook J, Fritsch E, Maniatis T. *Molecular Cloning: A Laboratory Manual* (1982) Cold Spring Harbor Laboratory Press, Cold Spring Harbor, N.Y.

Sanger F, Nicklen S, Coulson A R. *Proc. Natl. Acad. Sci. USA* (1977) 74:5463-5467

Sato K, Okamoto H, Aihara S, Hoshi Y, Tanaka T, Mishiro S. *Virology* (1993) 196:354-357

Schalich, J., S. L. Allison, K. Stiasny, C. W. Mandl, C. Kunz, and F. X. Heinz. 1996. Recombinant subviral particles from tick-borne encephalitis virus are fusogenic and provide a model system for studying flavivirus envelope glycoprotein functions. *J Virol* 70:4549-57

Scott J K, Smith G P. *Science* (1990) 249:386-390

Thomssen, R., S. Bonk, C. Propfe, K. H. Heermann, H. G. Kochel, and A. Uy. 1992. Association of hepatitis C virus in human sera with beta-lipoprotein. *Med Microbiol Immunol* (Berl) 181:293-300.

Wellnitz, S., B. Klumpp, H. Barth, S. Ito, E. Depla, J. Dubuisson, H. E. Blum, and T. F. Baumert. 2002. Binding of hepatitis C virus-like particles derived from infectious clone H77C to defined human cell lines. *J Virol* 76:1181-93.

Yagnik A T, Lahm A, Meola A, Roccasecca R M, Ercole B B, Nicosia A, Tramontano A. *Proteins* (2000) 40:355-366

Yoshikura, H., M. Hijikata, N. Nakajima, and Y. K. Shimizu. 1996. Replication of hepatitis C virus. *J Viral Hepat* 3:3-10.

Young K K, Resnick R M, Myers T W. *J. Clin. Microbiol.* (1993) 31:882-886

The invention claimed is:

1. A humanized antibody comprising an antigen-binding fragment of an antibody secreted by the hybridoma deposited under the accession number CNCM I-2983 or CNCM-2982, wherein said antigen-binding fragment of said antibody specifically binds HCV E1 or HCV E2 protein, respectively.

2. An antigen-binding fragment of an antibody secreted by the hybridoma deposited under the accession number CNCM I-2983 or CNCM I-2928, wherein said antigen-binding fragment is selected from the group consisting of Fab, F(ab')2 and scFv, and wherein said-antigen binding fragment of said antibody specifically binds HCV E1 or HCV E2 protein, respectively.

3. A composition comprising as active substance at least one antibody according to claim 1 and a pharmaceutically acceptable vehicle.

4. A composition comprising as active substance at least one antigen-binding fragment according to claim 2 and a pharmaceutically acceptable vehicle.

* * * * *